US012752051B1

(12) United States Patent
Friesen et al.

(10) Patent No.: US 12,752,051 B1
(45) Date of Patent: Oct. 6, 2026

(54) CRANIAL DRUG DELIVERY SYSTEM

(71) Applicant: CraniUS LLC, Baltimore, MD (US)

(72) Inventors: Owen Friesen, Baltimore, MD (US); Basile Michelet, Baltimore, MD (US); Josiah Verkaik, Baltimore, MD (US); Joshua Schaefer, Baltimore, MD (US); Parker Treadway, Baltimore, MD (US); Peter Lord, Baltimore, MD (US); Richard Purvis, Baltimore, MD (US); Eric Chappel, Baltimore, MD (US); Fanny Oddon, Baltimore, MD (US); Pierre Thiebaud, Baltimore, MD (US); Chad Gordon, Baltimore, MD (US); Bejan Darbandi, Baltimore, MD (US); Natalie Wisniewski, Baltimore, MD (US)

(73) Assignee: CraniUS LLC, Baltimore, MD (US)

( * ) Notice: Subject to any disclaimer, the term of this patent is extended or adjusted under 35 U.S.C. 154(b) by 0 days.

(21) Appl. No.: 19/346,681

(22) Filed: Oct. 1, 2025

Related U.S. Application Data

(60) Provisional application No. 63/715,786, filed on Nov. 4, 2024.

(51) Int. Cl.
*A61M 5/142* (2006.01)
*A61F 2/28* (2006.01)
*A61M 5/155* (2006.01)

(52) U.S. Cl.
CPC ....... *A61M 5/14276* (2013.01); *A61F 2/2875* (2013.01); *A61M 5/155* (2013.01); *A61F 2002/2817* (2013.01); *A61F 2310/00023* (2013.01); *A61M 2205/02* (2013.01); *A61M 2205/04* (2013.01); *A61M 2210/02* (2013.01); *A61M 2210/0687* (2013.01)

(58) Field of Classification Search
CPC .............. A61M 5/14276; A61M 5/155; A61M 2205/02; A61M 2205/04; A61M 2210/02; A61M 2210/0687; A61F 2/2875; A61F 2002/2817; A61F 2310/00023
See application file for complete search history.

(56) References Cited

U.S. PATENT DOCUMENTS

| | | | |
|---|---|---|---|
| 5,385,582 A | 1/1995 | Ommaya | |
| 5,978,701 A | 11/1999 | Johnson et al. | |
| 6,056,725 A | 5/2000 | Elsberry | |
| 6,093,180 A | 7/2000 | Elsberry | |

(Continued)

FOREIGN PATENT DOCUMENTS

| | | |
|---|---|---|
| CN | 115591048 B | 3/2023 |
| EP | 4181780 B1 | 7/2025 |

(Continued)

*Primary Examiner* — Leslie A Lopez
(74) *Attorney, Agent, or Firm* — Maier & Maier, PLLC

(57) ABSTRACT

According to one or more embodiments a medical implant housing may be provided. The medical implant housing may include a reconstructive medical implant that replaces missing bone and/or soft tissue, a fluid delivered by the reconstructive medical implant, a two-phase propellant, a pump that maintains a constant infusion pressure of the fluid via the two-phase propellant, and a mechanical flow regulator configured to maintain a constant flow rate. The medical implant housing may further include at least one catheter to deliver the fluid to a target site.

7 Claims, 14 Drawing Sheets

(56) References Cited

U.S. PATENT DOCUMENTS

| | | | | |
|---|---|---|---|---|
| 6,594,880 | B2 | 7/2003 | Elsberry | |
| 6,893,429 | B2 | 5/2005 | Petersen | |
| 7,662,140 | B2 | 2/2010 | Heruth et al. | |
| 9,452,241 | B2 | 9/2016 | Gill et al. | |
| 10,518,075 | B2 | 12/2019 | Gill | |
| 11,534,592 | B2 | 12/2022 | Singh et al. | |
| 11,730,923 | B2 | 8/2023 | Imran | |
| 11,992,642 | B2 | 5/2024 | Bodner | |
| 2017/0172961 | A1* | 6/2017 | Heller | A61K 9/0097 |
| 2019/0269850 | A1* | 9/2019 | Shih | A61M 5/16881 |
| 2022/0296868 | A1 | 9/2022 | Incube | |
| 2023/0071660 | A1 | 3/2023 | Spehr et al. | |
| 2023/0091409 | A1 | 3/2023 | Abrams et al. | |
| 2023/0097082 | A1 | 3/2023 | Muckenhuber | |
| 2023/0173418 | A1* | 6/2023 | Logothetidis | A62B 23/02 128/863 |
| 2023/0302255 | A1 | 9/2023 | Piferi | |
| 2025/0332340 | A1 | 10/2025 | Trieu | |

FOREIGN PATENT DOCUMENTS

| | | | |
|---|---|---|---|
| JP | 2009535155 | A | 10/2009 |
| JP | 6498613 | B2 | 4/2019 |

* cited by examiner

CRANIAL DRUG DELIVERY SYSTEM

BACKGROUND

Effective treatment of many central nervous system (CNS) diseases is limited by the blood-brain barrier (BBB), which prevents most systemically administered drugs from reaching brain tissue at therapeutic levels. High systemic doses are often required to achieve minimal brain penetration, leading to off-target toxicity (BTRT). There is therefore a critical clinical need for intracranial drug delivery that enables direct delivery of medications (e.g., chemotherapeutics, antibiotics, anti-inflammatories, or neuromodulators) to brain tissue or cerebrospinal fluid. Localized delivery bypasses the BBB and can dramatically increase drug concentration at the target site while minimizing systemic side effects. For conditions like malignant brain tumors (e.g., glioblastoma), chronic infections, or refractory neurological disorders, controlled intracranial infusion offers the promise of improved efficacy by maintaining therapeutic drug levels in the brain over extended periods. Furthermore, the life expectancy for patients with malignant brain tumors such as Glioblastoma is relatively the same as it was 50 years ago, in light of billions and billions of being spent of drug research. As such, the origin of chronic brain disease is more of a delivery problem, than it is an actual drug problem.

Many prior art drug pumps and reservoirs exist, but most are not appropriate for delivering a therapeutic agent to the cranial space. There have been a handful of devices aimed at providing drug delivery to the brain. However, these have significant limitations and disadvantages.

One of the earliest and most widely used implantable systems for intracranial drug delivery is the Ommaya reservoir (pertaining to U.S. Pat. No. 5,385,582), introduced in 1963 as a ventricular access device. The Ommaya reservoir consists of a small dome-shaped chamber (about the size of a quarter) that is implanted beneath the scalp (typically on the outer skull surface) and connected to an intraventricular catheter. This allows for repeated percutaneous injections of therapeutic agents directly into the cerebrospinal fluid, enabling intrathecal drug delivery without repeated lumbar punctures. However, these reservoirs have inherent limitations. The internal reservoir volume is small (typically on the order of ~1.5-2.4 mL in adult versions), and the larger volumes typically administered (5-10 mL) are injected via syringes in a single bolus by the clinician in a rapid (seconds to minutes) and uncontrolled fashion (variable depending on the clinician). CSF fluid turns over every 4-6 hours, and hence the drug is rapidly cleared. This necessitates frequent injections to maintain therapeutic doses for ongoing therapy. Rapid infusion of several mL of fluid can cause dizziness and nausea in patients. Compliance is low for patients who need to receive frequent injections, and even twice-weekly injections are difficult for patients and clinicians to keep up with. Furthermore, there is no reservoir included within the design and so there is zero ability for one to withdraw any volume of medicine once injected, even if and when unexpected symptoms were to develop such as headache, nausea, vomiting, seizures, and/or severe allergic response.

Another class of prior art comprises fully implantable infusion pump systems that can deliver drugs to the intrathecal or intracerebral space at programmable rates. A notable example is the Medtronic SynchroMed™ series of pumps, which have been used for decades to treat chronic pain or spasticity via intrathecal drug infusion and have also been adapted for intracranial drug delivery in clinical trials. These pumps typically reside in a subcutaneous pocket in the patient's torso (e.g., the abdominal wall) and contain an internal reservoir (available in sizes of ~20 mL or 40 mL) and a battery-powered programmable pump mechanism. The pump connects to the target site in the CNS through a long and flexible catheter tunneled under the skin for several feet. For brain applications, the catheter may be threaded up from the chest or abdomen, through the neck, and into the cranium to reach an intraventricular or intraparenchymal location. Because of the required length described above, it is often a surgeon's struggle to prevent any sort of catheter kinking or malposition to assure proper flow. This is disclosed in U.S. Pat. Nos. 5,978,701, 6,056,725, 6,093,180, 6,594,880, and 6,893,429. This architecture enables continuous or intermittent drug infusions to the brain over weeks or months with precise flow rate control, thereby addressing the limitation of pulsed bolus delivery seen in simple Ommaya-type reservoirs. However, this type of system was initially design and invented for spinal cord usage, and not for brain-related applications. As such, there is an inherent disadvantage when it comes to relative component size and materials chosen; since the space within the human torso/subcutaneous pocket/spinal canal is exponentially larger than the space within the skull/scalp/brain. Furthermore, spinal cord imaging is not at risk with regional placement along the torso due to the geographic size involved-specifically when it comes to detrimental radiological artifact and suboptimal radiographic imaging.

Despite these advantages, traditional implantable pump systems present their own challenges when repurposed for intracranial drug delivery. Because the pump unit is relatively bulky (designed for implantation in the torso), it cannot be situated near the brain; instead, it relies on a remote reservoir location and lengthy catheter (ie. >2-3 feet long) tubing to bridge the distance to the cranial site. This remote configuration can be suboptimal anatomically and functionally. The long catheter coursing from the pump to the brain must traverse the neck and subgaleal space, which introduces risks of kinking, migration, and/or disconnection over time. Indeed, catheter-related complications (blockage, tearing, and/or malposition) are a well-documented failure mode in intrathecal pump therapy. The presence of extensive tubing also creates potential dead space and may complicate precision flow and pressure management; for example, changes in posture could affect hydrostatic pressure in the line, potentially influencing infusion dynamics at the brain delivery site.

More recently, U.S. Pat. No. 7,662,140 describes an alternative route for drug delivery to the head from a remote drug pump using a subarachnoid approach. The "140" patent references US2003/0097082 entitled "Methods and apparatuses for navigating the subarachnoid space," another reference for this approach. Catheterization within the subarachnoid space of the spine is thought to have overcome some of the disadvantages of remote delivery through the neck, including infection risk, mechanical stress, and complications associated with kinking, migration, obstruction, or inadvertent dislodgement. Additionally, the subarachnoid approach avoids the occurrence of visible or palpable external tubing. However, by using a remote drug pump outside the confines of the skull, one again is challenged with the length of the tubing and the obstacles of achieving flow rate precision.

A primary disadvantage of delivering drugs via the subarachnoid approach, as described in the '140 patent, is that it relies on the passive circulation of cerebrospinal fluid (CSF) for drug distribution. The invention provides a method of delivering a drug to a subject's brain via the subject's spinal column. The method involves administering a hypobaric solution comprising the drug to the subject's cerebrospinal fluid (CSF) in the subject's spinal column. Buoyant forces will cause the drug to rise through the CSF into the subject's brain. The drug may be administered at a spinal location near the brain to facilitate the entry of the drug into the brain. Consequently, this method inherently lacks precise control over drug localization, making it unsuitable for targeting specific, localized pathologies such as tumors. Because drug dispersion in the subarachnoid space depends on CSF circulation patterns, therapeutic agents become broadly distributed rather than concentrated at precise anatomical sites. Thus, this method is significantly limited in effectively addressing focal lesions or localized abnormalities, such as tumors, cysts, or distinct pathological tissue areas. Moreover, the diffuse nature of drug distribution increases the exposure of healthy brain tissues to therapeutic agents, heightening the risk of unintended side effects. Lastly, the subarachnoid space inhibits the approach known as "convection-enhanced delivery" (CED). Notably, CED requires a pressure gradient at the distal catheter tip, and something that is only possible by placing the catheter in the parenchyma itself, and not the subarachnoid space.

Another limitation of all remote pump configurations (pump in the abdomen far from the brain) is that the pump unit is in a location such as the abdomen, separate from the cranial anatomy. This suboptimal anatomical accommodation means that the therapeutic hardware is not consolidated near the disease site; in some cases, patients may even feel discomfort or pain around the implanted pump in the torso, or encounter issues such as pump flip/dislodgment if the securing sutures or pocket are compromised. As such, this surgical approach requires two separate surgical incisions as opposed to a single incision, and thus the risks for surgical site infection and incision-related complications is doubled. Another significant drawback of remote pump configurations is the frequent requirement for a second-stage or extended surgical procedure. In typical clinical workflows, the initial cranial procedure (such as tumor resection or catheter placement) is completed first through a single incisional approach, after which the patient must undergo a separate, staged implantation of the drug pump in a remote body cavity (e.g., the abdomen). This necessitates additional anesthesia, operating room time, and perioperative risk. In summary, while implantable pump systems provide controlled drug infusion and larger drug reservoirs, they still rely on a remote, body-mounted reservoir and long catheter lines, which pose challenges in terms of anatomical integration, convenience, and long-term reliability for brain-targeted therapy. Importantly, the blood supply to the subcutaneous space within the torso is exponentially lower than the blood supply to the skull and scalp space, and because of this, the risk of infection is higher simply because of the body's limited delivery of white blood cells and perioperative antibiotics.

Despite various attempts over the decades to refine intracranial drug delivery platforms, a fully integrated, anatomically conformal system has yet to be widely adopted in clinical practice. Most existing systems represent either legacy solutions adapted from other anatomical targets or incremental improvements to older architectures that fail to resolve core limitations. These include poor anatomical integration, cumbersome form factors, insufficient reservoir capacity, and limited dosing precision. Traditional device designs often treat drug delivery and cranial reconstruction as separate surgical concerns. Recent efforts in the field are directed toward an integrated solution.

Despite their advantages, propellant-driven bellows pumps in the prior art have historically faced limitations in achieving precise, reproducible control of flow, particularly at the ultra-low flow rates required for certain neurological and intrathecal applications. Traditional systems often relied on fixed microbore capillary tubes, porous plugs, or precision laser-drilled orifices as passive flow restrictors. While these methods provide a degree of flow resistance, they are inherently sensitive to variations in fluid viscosity, temperature, backpressure, and even particulate contamination. More advanced systems introduced controlled valves and magnetic actuation to modulate flow with greater precision, but this came at the expense of increased system complexity, power requirements, and electromechanical failure points. Moreover, most historical systems were not equipped to deliver drugs directly into the brain parenchyma, where microflow stability and resistance to retrograde flow are paramount.

SUMMARY

According to one or more exemplary embodiments an implantable, refillable drug delivery system specifically designed for intracranial administration of therapeutic agents may be provided. It comprises a compact, bellows-type reservoir with a hermetically sealed propellant chamber integrated within a cranial prosthesis for precise, controlled, and sustained drug infusion directly into targeted brain tissues. The integrated drug-delivery system utilizes a carefully selected, low-vapor-pressure, two-phase propellant that applies consistent operating pressure to a flexible metal bellows.

A critical feature of the device is its miniaturized regulator assembly, containing MEMS-based flow regulator chips positioned downstream of the reservoir. These regulator chips work synergistically with the bellows mechanism, precisely controlling drug delivery rates by compensating for variations in reservoir and exit pressure.

The system includes thin-walled titanium reservoir and regulator enclosures sealed by laser welding, a sintered titanium microfilter for excluding particulates and bacteria, and a robust septum interface for minimally invasive, repeated refilling through percutaneous needle access. Biocompatible polymer casings, preferably constructed from PEEK or comparable thermoplastics, ensure structural integrity, biocompatibility, and MRI compatibility. The clamshell casing maximizes internal volume utilization, enhances structural rigidity, and simplifies assembly and sealing. Internal epoxy filling and redundant elastomeric seals provide additional mechanical reinforcement and ensure fluid containment.

A notable advantage of the invention is its substantial reservoir capacity, which is approximately 8 cc or greater, a considerable amount for a reservoir positioned in close proximity to brain tissue. This increased reservoir volume reduces the frequency of refills required and decreases associated clinical risks by limiting the need for repeated invasive access, thereby enhancing both patient comfort and safety in long-term therapeutic applications. Notably, larger reservoir size dictates a larger footprint, while a small reservoir size allows for a smaller footprint—and this must be accounted for when considering frequency of use and/or the practice of medicine.

Overall, the embodiments may be understood to offer a comprehensive, anatomically-tailored solution for sustained intracranial drug delivery, integrating structural protection, aesthetic restoration consistent with Neuroplastic Surgery principles aimed at avoiding social stigma and visual deformity, precision-controlled infusion, and MRI-compatibility. It effectively addresses critical challenges associated with localized neurological treatments, providing precise dosing, minimal invasiveness, consistent long-term performance, and seamless compatibility with standard surgical, sterilization, and postoperative imaging protocols, thereby significantly enhancing patient safety, efficacy, and quality of life.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Each figure and its corresponding description herein serve to fully disclose and illustrate the structural and functional details of the invention, enabling those skilled in the art to understand and practice the invention.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Furthermore, to facilitate an understanding of the description, a discussion of several terms used herein follows.

As used herein, the word “exemplary” means “serving as an example, instance, or illustration.” The embodiments described herein are not limiting, but rather are exemplary only. It should be understood that the described embodiments are not necessarily to be construed as preferred or advantageous over other embodiments. Moreover, the terms “embodiments of the invention”, “embodiments” or “invention” do not require that all embodiments of the invention include the discussed feature, advantage, or mode of operation.

In one or more exemplary embodiment a cranial drug delivery system may be provided.

Figure 1:
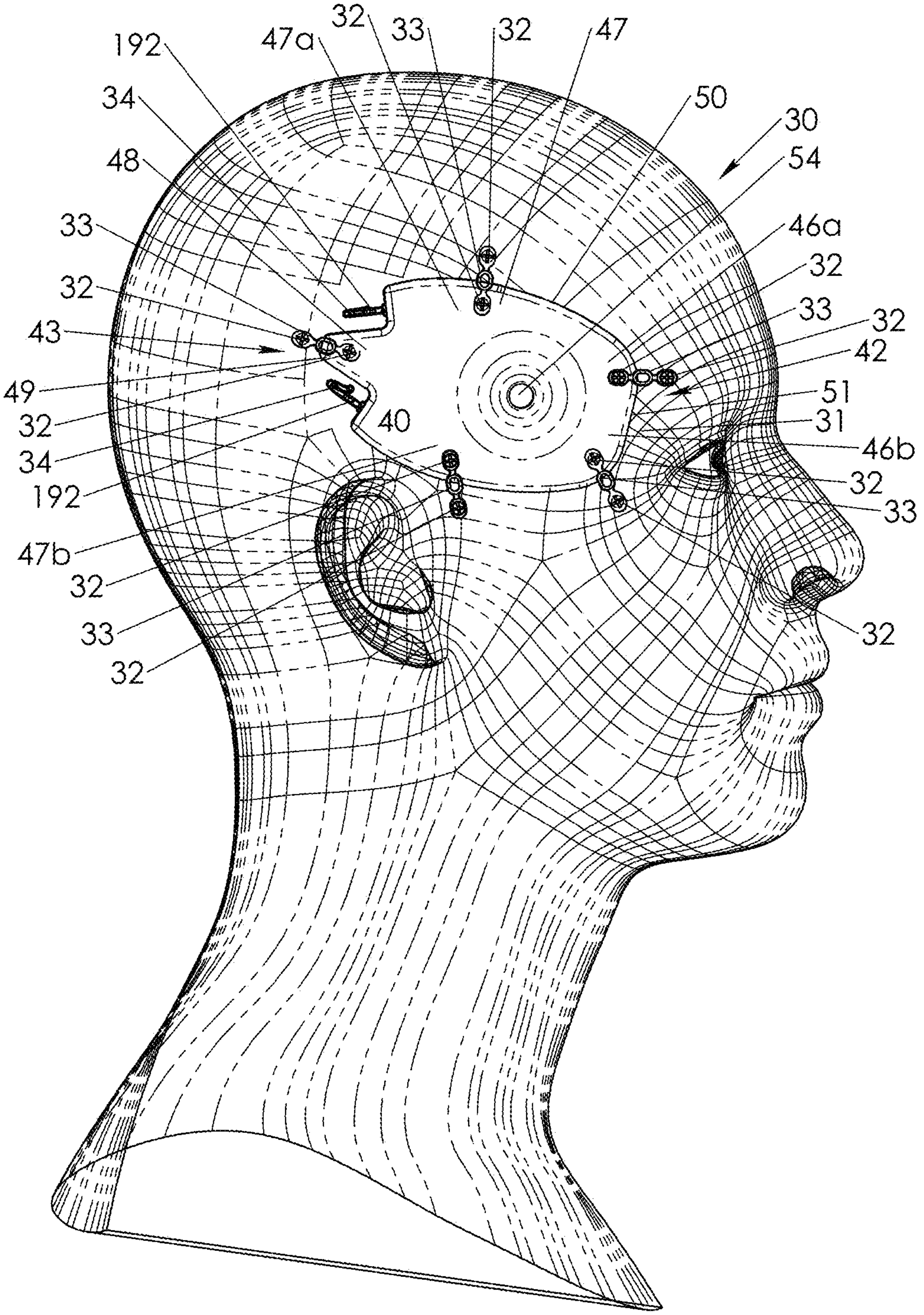
FIG. 1 is a generic representation of the cranial drug pump prosthesis in its approximate anatomical position relative to the human head according to an exemplary embodiment.

Referring to FIG. 1, case 40 may be illustrated according to an approximate anatomical position and orientation relative to the right side of a human head model 30. The case 40 may have a generally elliptical boundary 50, characterized by being longer along its lateral aspect (long axis) and narrower in its vertical aspect (short axis). The posterior end 34 of case 40 may extend toward the rear portion of the head 30. At the anterior end 42, the elliptical boundary 50 may be interrupted at the anterior end by a planar shoulder 51, positioned in the temporal region 31, where the prosthesis exhibits a wider/blunter boundary for abutting in the temporal region 31. A fill port orifice 54 may be positioned near the center of case 40.

One or more catheters 34 (only shown in FIG. 1) may be used in conjunction with the device. The one or more catheters 34 may be small, flexible polymer tubes designed to convey fluid from catheter fitting interfaces 192 to a target site located deeper within the brain tissue. In one embodiment, the internal diameter of a catheter adapted to interface with the catheter fittings interface 192 may be approximately 0.7 mm, though it may vary significantly depending on specific clinical requirements and application parameters.

It may be understood that until recently, there have been no craniofacial skull-soft tissue implants pre-designed for the temporal region that incorporate a drug delivery system to deliver a therapeutic agent to the brain. One or more embodiments of the invention provide a cranial drug system that may be strategically designed to replace both the temporal hard (i.e., bone) and soft tissue (i.e., temporalis muscle, temporal fat pad, and subcutaneous tissue) simultaneously in a way that camouflages the device itself yet facilitates a large drug reservoir in the range of 7-10 cc. It may be understood that a device design compatible with combined hard and soft tissue spaces may enable sufficient device size to incorporate an integrated drug delivery system, by providing a much larger available volume compared to a prosthesis that only replaces bone structures. Maximizing the drug volume provided in the prosthesis may further extend the period of drug delivery and reduce the frequency of refilling.

It may be understood that systemic delivery of medication to the brain is hindered by the blood-brain barrier's highly selective permeability, which allows the passage of only certain materials from capillary blood into the brain's extracellular fluid, on its way to the subdural white matter itself. As such, much work has been focused on engineering medicinal compositions that are small and hydrophobic enough to diffuse through the endothelial cells that make up the blood-brain barrier. However, it may be understood that many medicinally advantageous compositions are simply too large or hydrophilic and cannot be engineered for such delivery to the brain.

In some embodiments, one or more embodiments of the cranial drug delivery device may employ a method of convection (i.e. pressure-driven flow) enhanced delivery (CED) to distribute medicine from a catheter into the white matter of the brain, so as to skip the blood vessel route altogether (ie. a synthetic blood vessel). One or more embodiments may therefore encompass a reliable method and device capable of chronic "convection-enhanced delivery" within the unique size constraints of the human head, but in a way that avoids visible deformity and/or asymmetry. Notably, it may be understood that given the thickness constraints of the device described here, this may be achieved by placing it within the temporal fossa region—where there is an abundant amount of soft tissue (temporalis muscle/temporal fat pad) overlying the hard tissue (bone).

Still referring to FIG. 1, in one or more embodiments, the device may be structurally coupled to the skull using, for example, a series of titanium bone plates 33 secured by bone screws 32. The bone plates 33 may bridge across the boundary of the device and may be secured at preferred anchor points to the skull. Allowable fixation zones to the device may include, for example, but not limited to, anterior fixation zones **46*a* and 46*b*, central fixation zones 47*a* and 47*b*, and posterior fixation zone 48. Of note, there may be specific fixation zones denoted since a piercing screw, placed unsafely, could disrupt the internal technology within—in instances where additional neurotech (sensors, batteries, wires, Bluetooth modules, wifi-connectivity hardware, etc) are to be placed. The outward facing shell may be preferably made of a polymer material such as PEEK, PMMA, porous polyethylene, or PPSU into which self-tapping screws may be directly screwed during implantation. The outer shell may be configured to be thicker around the boundary to facilitate the depth of bone screws secured thereto. Plates may be, for example, strips of perforated titanium to minimize the metallic volume. In some embodiments, four more plates may be used based on motion detecting in the OR during fixation. In an alternative embodiment, designed brackets may be employed for structural coupling of the case assembly 40** to the skull.

In addition to treating brain cancer patients, the embodiments may also find applications in chronic neurological disease states like neurodegenerative disease (i.e., Alzheimer's, Parkinson's), medicine-resistant epilepsy, neurotrauma/paralysis, major depression, schizophrenia, bipolar disease, ADHD in children, brain dysfunction (i.e., paralysis), brain related age-changes (i.e., memory loss), post-traumatic stress disorder, and/or brain-enhancement methodologies to counteract effects of aging. Also, future options may include stem cell injections via this device for enhanced brain recovery following traumatic brain injury, cancer or stroke, as well as brain-enhancing medicines or supplements that could increase one's memory, athletic performance, balance, hand-eye coordination, and/or high-stress situation performance (military, police, etc.).

It may be understood that in certain embodiments and for certain use cases, for example a malignant brain tumor patient who is getting imaged every 90-120 days for brain tumor recurrence, it may be imperative that the device is MRI-compatible in that there is no ferromagnetic material but also that it exhibits a minimal size MRI artifact (distortion in the image) that does not extend far from the device surfaces. Some embodiments may facilitate MRI images of surrounding brain tissue by minimizing the extent of metal (titanium) material that is used in the case assembly 40 and limiting the use of metal (preferably titanium) only to the thin-walled and drug-delivery system components and to small fasteners. Therefore in some embodiments a majority of the case volume may be a polymer material, and therefore the MRI artifact may be kept to a minimum. Additionally, most of the titanium mass may be strategically concentrated toward the outer shell of the device, such that the extent of the artifact that extends beyond the interior boundary of case 40 is minimized.

In one embodiment the case material may be preferably PEEK (Polyether ether ketone), a semi-crystalline, high-performance thermoplastic polymer known for its exceptional mechanical strength, chemical resistance, and biocompatibility. PEEK may be understood to be highly biocompatible, minimizing the risk of adverse reactions, rejection, or inflammation upon implantation, and demonstrates excellent resistance to chemical and biological degradation in physiological environments, making it well-suited for long-term biomedical applications. With a high strength-to-weight ratio, PEEK offers robust structural integrity without adding excessive mass, and its elastic modulus closely approximates that of cortical bone, enhancing its compatibility with surrounding anatomical structures.

Moreover, it may be understood that PEEK is transparent to MRI and other imaging modalities such as X-ray, CT and ultrasound, thereby facilitating improved postoperative imaging. The material may also be easily machinable and can be molded into complex geometries, allowing for the creation of patient-specific implants. Its resistance to hydrolysis, oxidation, and chemical degradation over extended periods ensures durability within the body. Finally, PEEK is compatible with standard sterilization techniques—including steam autoclave, gamma radiation, and ethylene oxide—ensuring sterility without compromising its mechanical or chemical properties.

The main tradeoffs with PEEK may be its cost and elevated melting point (approximately 370-400° C.), which may make it more challenging to process using conventional thermoplastic manufacturing methods. Additionally, PEEK presents specific challenges for bonding due to its inherent chemical resistance, high crystallinity, and low surface energy. These characteristics often necessitate specialized bonding techniques or surface treatments to achieve reliable adhesion.

In alternative embodiments other polymer options for the implant enclosures may include, for example, Polyphenylsulfone (PPSU), Polysulfone (PSU), Polyetherimide (PEI), and Polycarbonate (PC).

Figure 2:
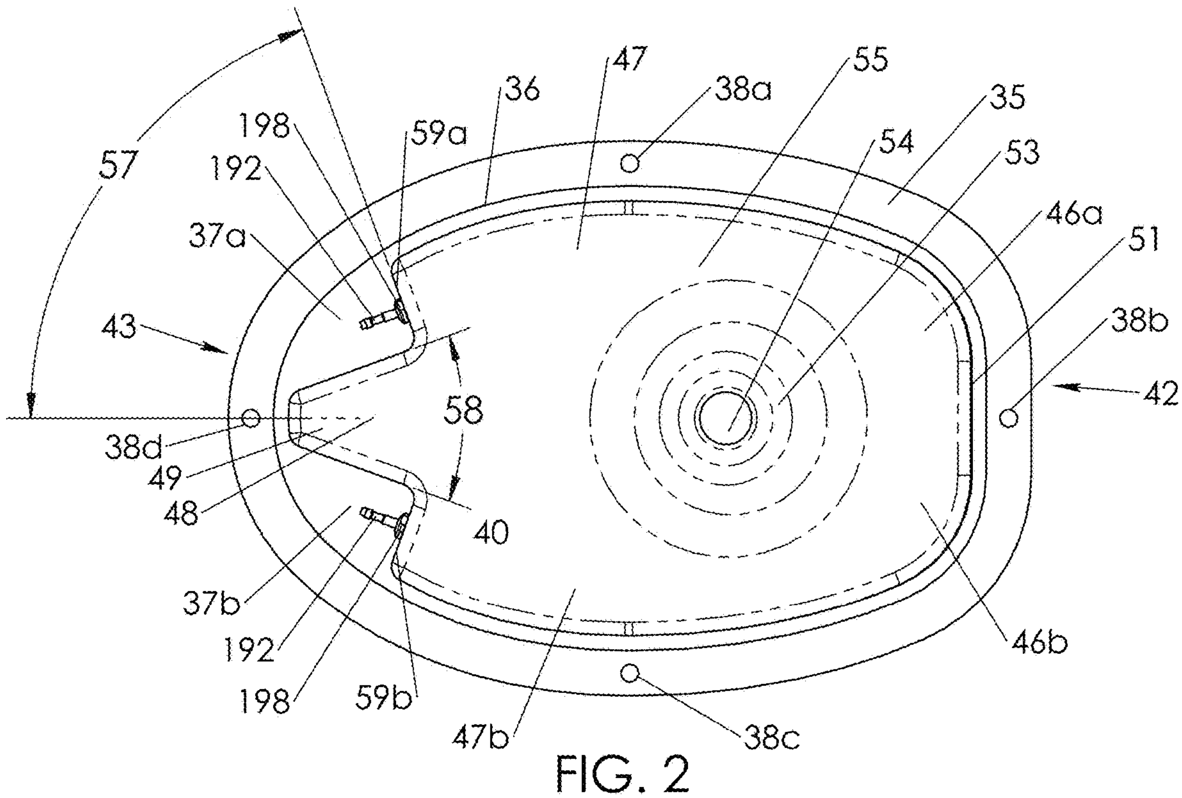
FIG. 2 is an orthogonal view of an exemplary embodiment of the device, normal to the outer shell, including a reference cutting guide.

Referring to FIG. 2, cutting guide 35 is shown to give an indication of the dissection boundary, and correspondingly, the boundary of the prosthesis according to an exemplary embodiment. As compared to the planar shoulder 51 of the anterior end 41, the posterior boundary may be more pointed (elliptical) but with recesses 37*a* and 37*b* for accommodating catheter attachment within the dissection boundary 36. Catheter recesses 37*a*-37*b* may be located on each lateral side, each of which may accommodate an instance of a catheter fitting interface 192 and catheter 34. Between these two catheter recesses 52, the posterior end 43 of the case 40 may form a nose protrusion 49, which may terminate at approximately the midpoint along the elliptical boundary's 50 long axis. According to the exemplary embodiment, the device may be adapted to fit within a generally elliptical region of dissected tissue that is approximately 91 mm long and 58 mm wide. In other embodiments the size of the dissected tissue may differ.

The drug delivery outputs of the device may be provided by the dedicated catheter fittings 192 positioned within strategically designed recesses 37*a* and 37*b* located near the posterior end 43 of the case. The recessed configuration may ensure that the catheter fitting interfaces 192 remain shrouded and protected within the dissected cranial space, thereby eliminating the risk of direct tissue impingement or abrasion. Catheter fitting interfaces 192 may be strategically located to minimize visible disruption (cosmetic defects). This placement near the posterior end, at 42, may enable the more visually prominent anterior region (near the temple) to be non-interrupted, thus maintaining aesthetic integrity where it is most critical (ie. non-hair bearing).

Recesses 37*a* and 37*b* may be intentionally designed to minimally interrupt the standard elliptical or dome-shaped profile of the prosthesis, preserving as much of the implant enclosure's external surface area as possible. This may maintain both structural support to the surrounding skull region and effective coverage over the brain. The geometry of the recesses may also incorporate adequate space and clearance to allow for effective routing and strain relief of the attached catheters. This integrated approach may promote stable catheter positioning and reduce mechanical stress on the tubing, thereby preventing catheter damage, kinking, or displacement.

The attachment of each catheter to each of the two catheter fittings 192 may occur within the respective catheter recesses 37*a* and 37*b*, enabling each fitting to be fully nested between the exterior and interior surfaces of case 40.

The implantation procedure may initially involve elevating the scalp flap with soft tissue above and dissecting a region of hard tissue (bone) defined by the internal boundary of a cutting guide 35. In instances where the patient has had previous brain surgery, the non-operated side pre-operative, CT scan imaging may help serve to best plan the desired implant thickness in custom fashion using quantitative analysis. The cutting guide 35 may comprise an internal dissection boundary 36 that may be offset, in an exemplary embodiment, approximately 3 mm outward relative to the boundary of the case 40. Specifically, the dissection boundary 36 may be offset by approximately 3 mm from the elliptical boundary that case 40 would exhibit if uninterrupted by the catheter recesses 37*a* and 37*b*. Consequently, the cutting guide 35 may present a generally elliptical configuration with a flattened end corresponding to the planar shoulder 51 at the anterior end 42 of the case 40. Additionally, fixation holes 38 may be provided in the cutting guide 35 to secure or reference the intended position of the cutting guide 35 during the marking of the boundary and/or during tissue dissection along the internal dissection boundary 36. The surgeon may remove any non-brain tissue, both hard and soft, to make room, while the brain is exposed underneath without injury.

In accordance with the exemplary embodiment, the geometry of the nose 49 may be defined relative to the geometry of the two symmetrical recesses 37. Specifically, the included angle 58 of the nose 49 may be approximately 40 degrees, while the catheter mounting angle 57 formed between the long axis and the locating surface of each catheter interface 192 may be approximately 70 degrees.

Figure 3:
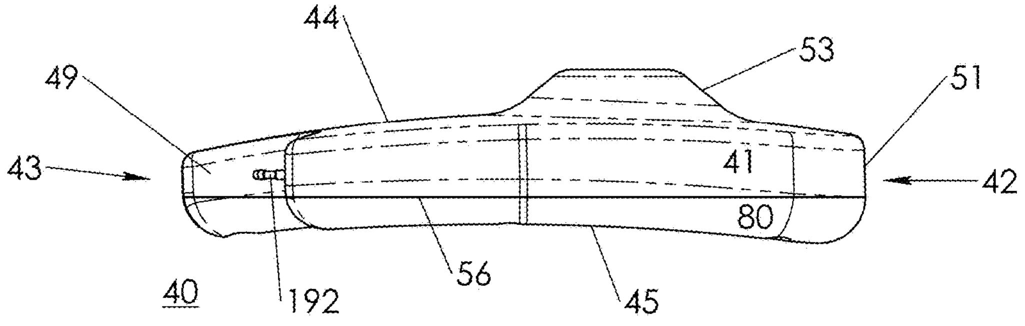
FIG. 3 is an orthogonal side view of an exemplary embodiment of the device, showing the device in its narrowest aspect.
Figure 4:
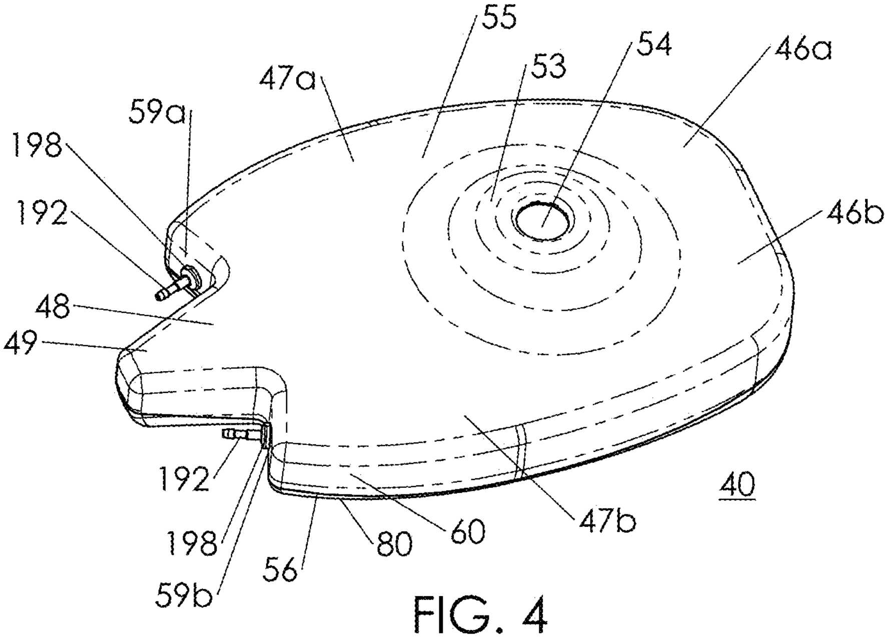
FIG. 4 is a perspective view of an exemplary embodiment of the device, oriented toward the outer shell.
Figure 5:
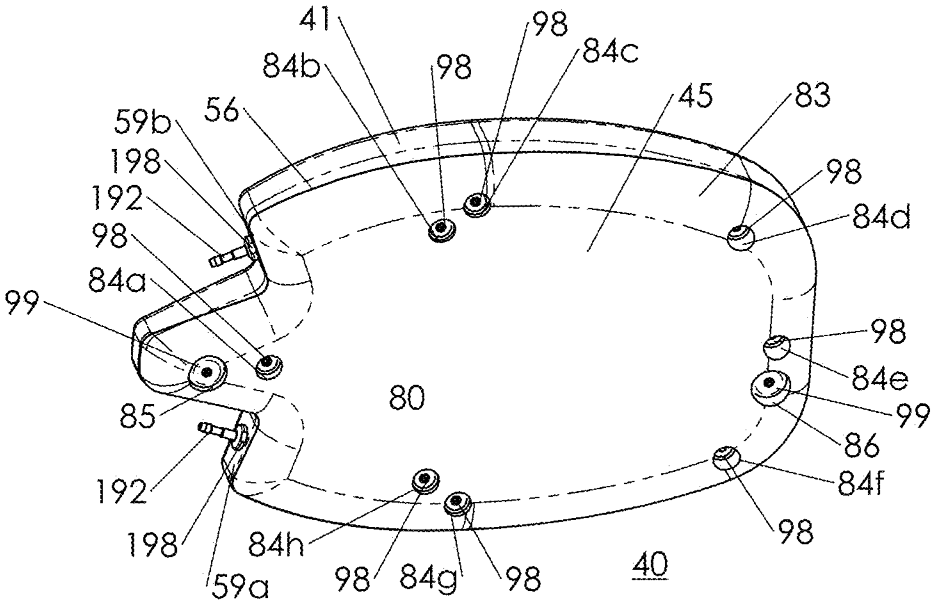
FIG. 5 is a perspective view of an exemplary embodiment of the device, oriented toward the inner shell.

Referring also to FIGS. 3-5, an exemplary embodiment of the case assembly 40 may be comprised of a two-part plastic clamshell housing consisting of an outer shell 41 and an inner shell 80 with parting line 56 at an intermediate position, which may dissect the entire boundary. With particular reference to FIG. 3, the outer shell 41 may feature a convex outer surface geometry corresponding to the pseudo-exocranial surface 44, and the inner shell 80 may exhibit a concave outer surface geometry corresponding to the pseudo-endocranial surface 45.

The exterior and interior geometry of the prosthesis may correspond to the void left by dissecting hard and soft tissue. The thicker anterior end 42 may be adapted for the temporal region, which is where anatomically-speaking, the human head has more room for technology implantation. The thinner posterior 43 end may extend toward the parietal region of the skull. Since the skull is generally spherical on the outside, the prosthesis may feature a spherical convex geometry corresponding to the exterior (pseudo-exocranial) surface 44, which may have a spherical radius of approximately 250 mm.

The dissected skull of the posterior region may be formally described as having an irregular, dome-like, or calvarial shape, exhibiting concave interior surfaces and convex exterior surfaces depending on the embodiment. Correspondingly, an exemplary prosthesis may exhibit concave interior geometry at the pseudo-endocranial surface 45 near the posterior end 43, with a spherical radius of approximately 250 mm and a thickness of approximately 12 mm in that region. Toward the anterior end 42, the depth of dissected soft tissue may increase, thus enabling the exemplary embodiment of the prosthesis to exhibit an increased thickness of 15 mm or more near the anterior end 42 (temporal region), which may be situated away from the concavity of the posterior end. Correspondingly, there may be more available depth to accommodate drug delivery system components near the anterior end 42 of the case 40. Following the described dissection, the case 40 may fit precisely within the resulting void, providing a small clearance around its boundary.

The outer shell 41 may further include circular features positioned within the central region of the pseudo-exocranial surface 44, offset toward the anterior end 42. These features may include a palpable nub 53 surrounding a fill port orifice 54, and associated markings 55 disposed around the palpable nub 53.

The palpable nub 53 may be an elevated, dome-like structure designed to enable tactile identification of the fill port orifice 54 through the scalp. This tactile feature may facilitate the precise insertion of a needle into the fill port orifice 54 for refilling an internal reservoir with liquid agent. The palpable nub 53 may have a conical profile at its base, transitioning to a smoothly rounded distal (protruding) end. This geometric configuration may be optimized for certain embodiments to reduce patient discomfort, minimize skin irritation, and mitigate the risk of tissue erosion. The overall protrusion height of the nub may range from approximately 6 to 8 mm, which may provide sufficient prominence for easy tactile identification beneath the skin. The size, height, and rounded shape of the palpable nub 53 may be engineered to support reliable and comfortable localization through the scalp, ensuring that needle insertion can be performed with precision and minimal pressure.

Fixation zones may be areas on the outer convex pseudo-exocranial surface 44 of the outer shell 41, which may allow for receiving self-drilling bone screws for fixation of the implant to the skull. Some embodiments may exhibit fixation zones distributed around the boundary of the prosthesis to enable fixation near the anterior end, posterior end, and near the mid-section of the implant for receiving four or more self-drilling bone screws in a distributed manner. These indicators may be implemented as, for example, surface markings, embossed features, or debossed features, and provide visual guidance to the surgeon regarding acceptable regions for the placement of bone screws.

Alternatively, a texturing process such as abrasive blasting may be applied to produce fixation zones with a surface finish that is visibly distinct from adjacent surfaces, resulting in a clear and intentional contrast. In the case of certain polymers, biocompatible inks may be used to print markings directly onto the surface, or other appropriate marking methods may be implemented depending on the material and application. For injection-molded components, the markings may be incorporated directly into the mold tooling so that the finished molded part exhibits the desired marking as an integral feature of its surface.

Provided on the pseudo-exocranial surface 44 of the outer shell 41 may be anterior fixation zone indicators 46*a* and 46*b*, central fixation zone indicators 47*a* and 47*b*, and/or a posterior fixation zone indicator 48. The anterior fixation zone indicators 46*a* and 46*b* may identify suitable regions on the case 40 near the anterior end 42 for securing self-drilling bone screws intended for attaching a bone plate as previously described in reference to FIG. 1.

The central fixation zone indicators 47*a* and 47*b* designate appropriate regions for the placement of self-tapping bone screws near the midsection of the case 40, while the posterior fixation zone indicator 48, located on the nose 49, may indicate an acceptable region for securing self-drilling bone screws and associated bone plates near the posterior end 43 of case 40.

The aforementioned fixation zones may provide suitable locations for the attachment of self-drilling bone screws, as these areas may be free of internal interfering structures and feature adequate wall thickness in the outer shell 41 to reliably accommodate bone screws. In some embodiments, the bone screws may be approximately 4 mm in length. Since these fixation regions define general zones rather than discrete points, flexibility may be provided concerning the precise placement of bone screws and fixation plates within each identified region given that the exact skull shape may have some slight variations versus the pre-operative imaging.

One or more of catheter fittings 190 may be attached to mounting shoulders 59*a* and 59*b* using one or more nuts 198 to provide a secure coupling to the case 40. The further integration of components for the drug delivery device will become apparent in reference to further description in other figures.

Referring now to FIG. 5, in an exemplary embodiment, the inner shell 80 and outer shell 41 may be joined together using multiple screws 98. These screws 98 may be inserted through the outer surface of the inner shell 80, arranged in a distributed pattern and offset inward from the boundary along the perimeter of the pseudo-endocranial surface 45. Additionally, two occurrences of fill port screws 99 may be situated near the boundary of the pseudo-endocranial surface 45 of the inner shell 80, facilitating an access port for filling or venting the internal cavities of the case 40 at both the anterior end and at the posterior end.

According to an exemplary embodiment, eight screws 98 may be seated within corresponding counterbores 84*a*-84*h*, which may or may not be back-filled with silicone after attachment. Additionally, a fill port screw 99 may be seated within an anterior fill port counterbore 86, and another fill port screw 99 may be seated within a posterior fill port counterbore 85. Following assembly and epoxy filling of the case 40, these counterbores are preferably but not necessarily back-filled with silicone. It may be understood that in other embodiments, a different number of screws may be used.

In an exemplary embodiment, a feature of the boundary geometry of the inner shell 80 may be the boundary fillet 83, which may fully surround the pseudo-endocranial surface 81 and may continuously extend along its entire perimeter. The boundary fillet 83 may have a sufficiently large radius (for example about 6 mm) to eliminate sharp edges or corners that might otherwise come into contact with or irritate sensitive anatomical structures.

In the exemplary embodiment, the outer shell 41 may be thicker and incorporate cavities for accommodating internal fluidic components, while the inner shell 80 may be thinner and function essentially like a cover to enclose drug delivery components seated into the outer shell 41. In an alternative embodiment, the parting line 56 may be moved to a position that more equally divides the two shells so that both shells incorporate cavities for accommodating internal fluidic components of the drug delivery system.

Figure 6:
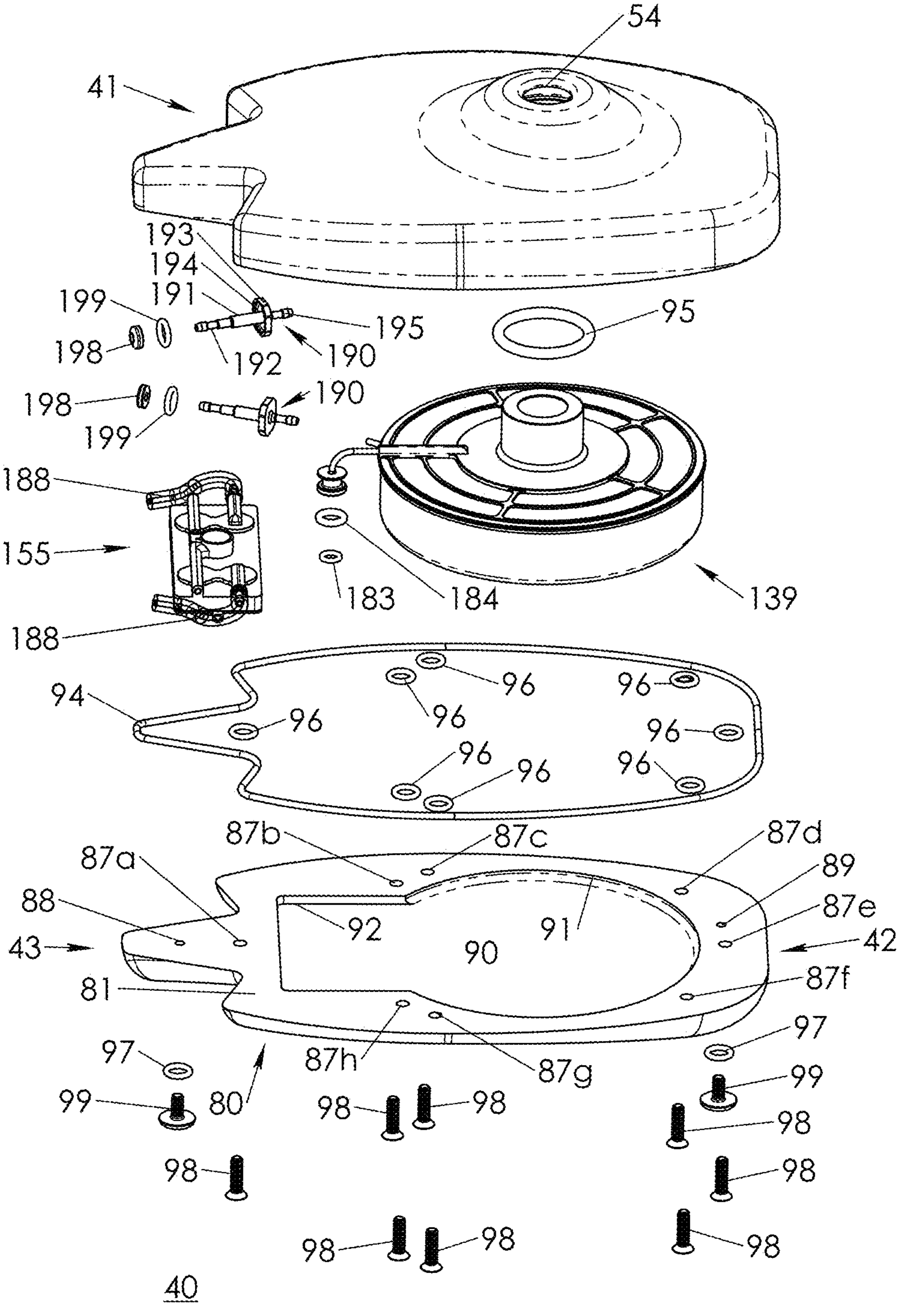
FIG. 6 is an exploded view of the case assembly according to an exemplary embodiment, showing additional features pertaining to the inner shell.

Referring now to FIG. 6, an exploded view illustrates the components of the case as well as those of the drug delivery system, in accordance with an exemplary embodiment. The illustrated drug delivery system components may include, for example, a reservoir assembly 139, an adapter axial O-ring 183, an adapter radial O-ring 184, a regulator assembly 155, two instances of flexible tubing 188, and two instances of catheter fittings 190. The reservoir assembly 139 connects to the regulator assembly 155 via a plug-and-socket interface, wherein the adapter axial O-ring 183 and the adapter radial O-ring 184 may provide redundant sealing between these interfacing assemblies.

Each catheter fitting 190 may comprise an internal tube interface 195 located at its proximal (upstream) end and a catheter interface 192 at its distal (downstream) end. Both interfaces may be configured as barb-type connections suitable for secure attachment to elastomeric tubing. Near the proximal end, each catheter fitting 190 may further include a flange 193 featuring an axial groove 194 positioned on its lateral surface to engage with the wall of the outer shell 41. The axial groove 194 may accommodate an O-ring 199 to create a fluid-tight seal near side holes 67*a* and 67*b* of the outer shell 41. When the catheter fittings 190 are secured to outer shell 41 through the side holes 67*a* and 67*b* (illustrated in FIG. 7), the O-ring 199 may be axially compressed, establishing an effective seal between the flange 193 and the adjacent internal surface of outer shell 41.

Each catheter fitting 190 may further include a threaded portion 191 (threads not shown) configured to receive a corresponding nut 198, which may be advanced into engagement with the external surface of the outer shell 41. The nut 198 may include an internal thread and an outer diameter (OD) with opposing flats that facilitate engagement by a wrench-like tool. This design may enable the nut 198 to be securely tightened, ensuring rigid fixation of each catheter fitting 190 to the case 40.

The two-part case 40 may comprise an outer shell 41 and an inner shell 80. According to an exemplary embodiment, eight screws 98 may be utilized to securely fasten the inner shell 80 to the outer shell 41 through screw holes 87*a*-87*h*. To ensure sealing around each through-hole, eight corresponding O-rings 96 may be positioned between the outer shell 41 and the inner shell 80 at each screw location. Additionally, a gasket 94 may provide a continuous seal along the outer boundary between the outer shell 41 and the inner shell 80. Furthermore, an O-ring 95 may provide a radial seal within the outer shell 41, creating a sealed interface against the reservoir assembly 139 at a position offset from, but proximal to, the fill port orifice 54. In other embodiments, a different number of screw and screw holes may be utilized.

According to an exemplary embodiment, the inner shell 80 is secured to the outer shell 41 with a series of screws 98 incrementally positioned around the case boundary for optimal structural coupling of the two halves together. Case screws 98 may be inserted through the inner shell and attach to blind threaded holes 62 on the inward-facing side of the outer shell 41 (shown in FIG. 7). In the exemplary embodiment, screws may be M1.6×0.35 thread and have a flat head with a Torx drive interface. The eight screws 98 may be employed in a distributed pattern at locations that do not interfere with internal drug delivery system components or with fixation zone regions. Because the small size and mass of the screws 98 minimizes the MRI artifact, in an exemplary embodiment the screws 98 may be titanium alloy (preferably Grade 23 TI6AL4V ELI). Case screws 98 may be employed in this embodiment as they provide a robust method of securing the clamshell halves together and resisting internal pressures applied to the shells by the drug delivery system during use and sterilization.

The following are alternative methods that can be employed to secure the enclosure halves according to other exemplary embodiments, each offering different advantages depending on structural, manufacturing, and material considerations. One approach may involve establishing a mechanically interlocking bead between the two halves through epoxy filling, creating a solid mechanical bond. Another method may be laser or ultrasonic welding, which may fuse the halves together at the molecular level, providing a strong, permanent joint. Solvent bonding may also be used, particularly when working with compatible thermoplastics. Mechanical fastening alternatives may include the use of snap-fit joint interfaces or locking clips, which allow for reassembly or simplified assembly without tools. Additional options include inserting set screws or dowel pins transversely across the joint to interlock the halves, employing rivets for permanent fastening, and/or using discrete tension elements secured by welded washers to maintain structural integrity. Each method presents unique tradeoffs in terms of strength, reworkability, material compatibility, and manufacturing complexity. It may be further understood the above list is non-limiting and non-exhaustive, and any other method known in the art may be utilized.

The clamshell case architecture may offer numerous advantages that contribute to both the mechanical performance and functional integration of the implant. The two-part clamshell design may inherently provide structural stiffness, as the joined halves mutually reinforce one another, forming a stable and rigid enclosure that effectively resists bending, twisting, and torsional loads. The symmetrical geometry of the clamshell may ensure even distribution of internal pressure applied to the distributed pattern of screws, reducing localized stress concentrations and potential failure points.

By maximizing the perimeter of the case, the clamshell design may afford extensive internal access, which may facilitate assembly, inspection, and precise placement of drug delivery system components. The rigid, interlocking halves may also provide exceptional physical protection against external mechanical impacts, vibration, and compression. The increased boundary length may offer additional space for accurate positioning of internal elements, including reservoir assembly 139, regulator assembly 155, and routing pathways. Moreover, dividing the enclosure along its narrowest dimension may ensure efficient use of internal volume and supports the compact integration of complex internal structures.

A key benefit of the clamshell approach may be the ability to position a sealing gasket 94 along the outward boundary of the case 40, where it maximizes internal space utilization. It may be understood that internal space utilization is a key advancement as every square centimeter of space utilized may need to be optimized in order to provide a seamless post-operative appearance with proper head symmetry, facial appearance, and zero surgical deformity. This may also allow for implementation of internal technology like biosensors, batteries, Bluetooth modules, Wifi connectivity, "smart" computer modules, etc. Assembly complexity may be understood to be reduced through the straightforward alignment and fit-up of internal components. Additionally, most internal cavities and positioning features may be substantially perpendicular to the parting surfaces, simplifying machining or molding processes. From an aesthetic perspective, the clamshell enclosure may provide a seamless and streamlined external appearance, with convex surface geometry and precisely aligned halves that eliminate prominent seams or gaps. Instances of case screws 98 and fill port screws 99 may be inserted from the underside of the implant, preserving the continuity of the external surface.

Alternative case architectures are feasible and may include various configurations depending on design priorities. Alternative embodiments may include an over-molded enclosure, in which portions of the case 40 are molded—for example using epoxy—directly over the internal components, with the molding process and tooling defining the external case geometry. Another approach may be deep-cavity enclosure, also referred to as a box-and-lid or tray-and-cover design, in which the enclosure is primarily formed by a single component containing a substantial internal cavity, closed off by a relatively thin or shallow lid. This architecture may emphasize the depth and internal volume afforded by the primary housing part.

A modular enclosure may also be employed, consisting of interlocking or interchangeable components that assemble into customizable structures. Alternatively, a frame and panel enclosure may involve mounting internal system components to a supporting internal frame, with two or more external panels attached to enclose the assembly.

Referring again to FIG. 6, the inner shell 80 may include a posterior fill port hole 88 positioned near the posterior end 43 and an anterior fill port hole 89 located near the anterior end 42. These fill port holes 88, 89 may be internally threaded to receive respective instances of fill port screws 99. After epoxy-filling of the case 40, each fill port screw 99 is installed to seal the corresponding threaded hole. Each fill port screw 99 has a "flanged (button-shaped) head" designed to compress an associated O-ring 97, which may establish an axial seal between the inner shell 80 and each fill port screw 99.

According to an exemplary embodiment, all threaded interfaces employed within the system may utilize M1.6×0.35 threads. This thread specification may provide a small yet robust connection suitable for secure structural attachment in components made of polyether ether ketone (PEEK).

FIG. 6 also illustrates internal details of the inner shell 80, which may be designed to accommodate one or more drug delivery components. Specifically, the inner shell 80 may include a central region defined by a planar parting surface 81, within which is formed a pocket 90. This pocket 90 may have a generally circular boundary 91 toward its anterior end and transitions into a rectangular boundary 92 toward its posterior end. The circular boundary 91 may be adapted to seat a reservoir assembly 139, while the rectangular boundary 92 is adapted for the accommodation of regulator housing 155.

Figure 7:
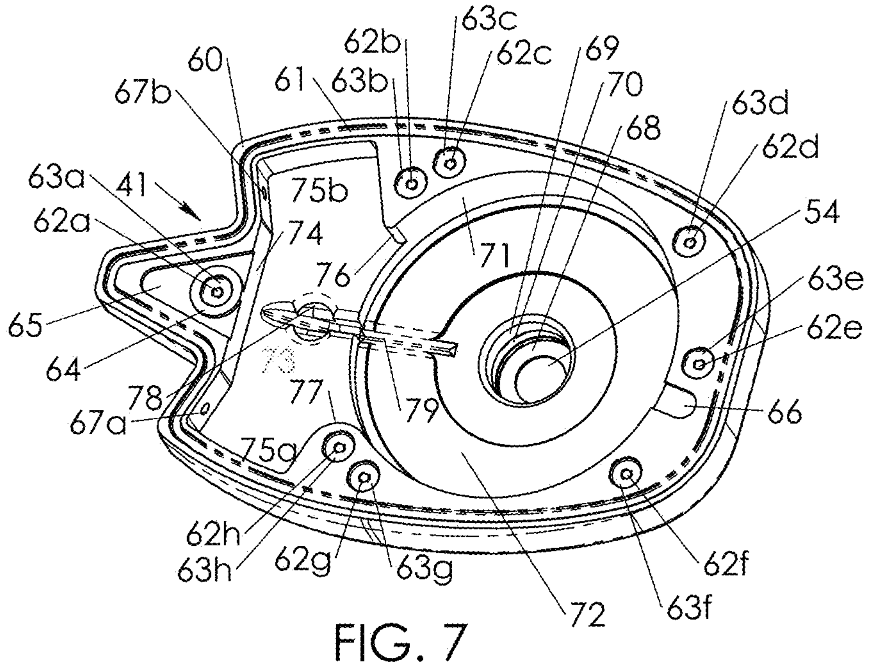
FIG. 7 is a perspective view of the outer shell according to an exemplary embodiment, oriented toward the internal cavities.
Figure 8:
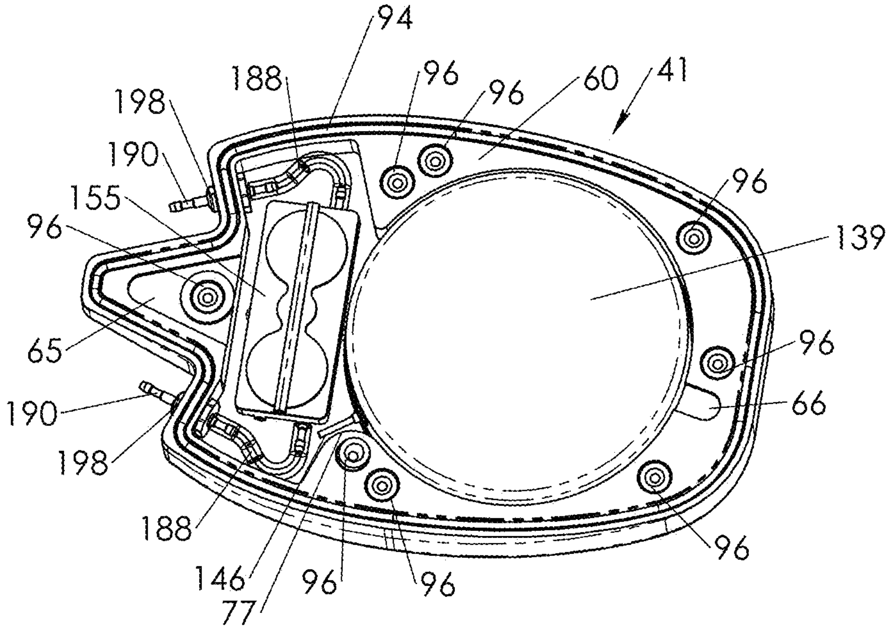
FIG. 8 is a perspective view of the outer shell in a similar orientation as FIG. 7, further incorporating the drug delivery system according to an exemplary embodiment.

Referring to FIGS. 7-8, perspective views are presented, oriented toward the planar parting surface 60 of the outer shell 41, highlighting internal features according to an exemplary embodiment. Specifically, FIG. 7 illustrates the outer shell 41 alone, while FIG. 8 shows the outer shell 41 integrated with components of the drug delivery system.

A gasket groove 61 may be formed in the outer shell 41 and may extend continuously along its entire perimeter. The groove 61 may be configured to seat a gasket 94, which, upon complete assembly of the case, may be compressed to ensure an effective seal along the outer boundary.

Eight threaded holes 62*a*-62*h* may be positioned around the planar parting surface 60, serving as fastening points for corresponding case screws 98. Each threaded hole 62*a*-62*h* may be surrounded by a respective counterbore 63*a*-63*h* designed to seat an O-ring 96, providing axial sealing between the outer shell 41 and the inner shell 80 upon compression during assembly. The interface created by these axial seals is further illustrated in FIGS. 22-23.

Within the inner region of the planar parting surface 60, pockets may be provided for accommodating the one or more drug delivery system components. A cylindrical pocket 71 may receive the larger cylindrical portion of reservoir assembly 139, while a header socket 69 may accommodate the smaller-diameter tubular portion. The cylindrical pocket 71 may further compress an annular depression 72 to provide increased axial clearance, as needed, to accommodate the reservoir assembly 139. A radial groove 70 positioned approximately midway along the header socket 69 may be configured to seat an O-ring establishing a fluid-tight seal between the outer shell 41 and the reservoir assembly 139, adjacent to the fill port orifice 54. Additionally, a header liner 68, defined by a thin-walled section of the outer shell 41, may serve to mask the titanium surfaces of the reservoir assembly 139, preventing external exposure. This configuration may ensure that any missed attempt at inserting a filling needle through the fill port orifice 54 may result in contact with the softer plastic material of the outer shell 41, rather than the harder titanium surface of the reservoir assembly 139.

Positioned toward the posterior end may be a posterior pocket 73, which may feature a perpendicular face 74 centrally located, and may further include additional pocket axillary zones 75*a* and 75*b* having non-orthogonal faces near the lateral sides. The posterior pocket 73 may be configured to accommodate the flow regulator assembly 155 centrally, while one or more instances of flexible tubing 188 reside within the pocket axillary zones 75*a* and 75*b*. Side holes 67*a* and 67*b* may intersect their corresponding pocket auxiliary zones 75*a* and 75*b*, facilitating passage and mounting of the two catheter fittings 190.

The one or more instances of flexible tubing 188 may interconnect the barb interfaces of the regulator assembly 155 and the catheter fittings 190. These flexible tubes 188 may serve as fluid conduits bridging the two interfaces, accommodating positional offsets and elevation differences between the regulator assembly 155 and the catheter fittings 190, within a confined spatial envelope. The wall thickness of each flexible tube 188 may be sufficient to facilitate a tight bend without the tube kinking. In an embodiment, the flexible tube 188 is silicone, but it may instead be Tygon or another suitable elastomeric material. Catheter fittings 190 may be secured to outer shell 41 using instances of nut 198, as was described previously in reference to FIG. 6. The posterior pocket 73 may partially intersect the cylindrical pocket 71, forming an intersecting edge between these two features. A transitional fillet may be provided along this intersecting edge, with a smaller fillet 76 situated on one side and a larger fillet 77 positioned on the opposite side. As shown in FIG. 8, the larger fillet 77 may provide sufficient space to accommodate the fill tube 146 of the reservoir assembly 139.

Figure 22:
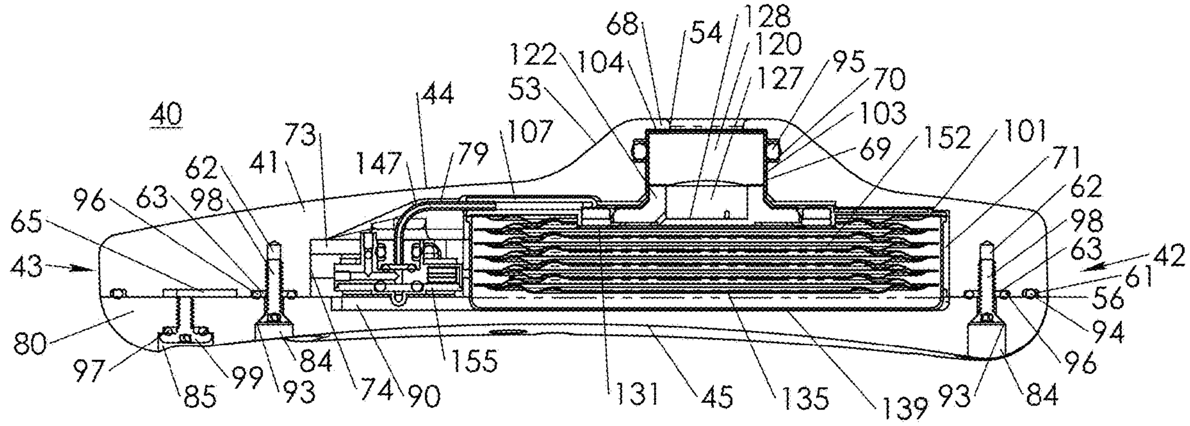
FIG. 22 is a mid-plane sectional view of the integrated case assembly according to an exemplary embodiment, taken along the long axis of the device.

A central slot 79 and cylindrical depression 78 may provide additional clearance where needed within the boundaries of cylindrical pocket 71 and posterior pocket 72 (best seen in reference to FIG. 22).

To provide fluid pathways allowing epoxy to flow between the fill port locations of the inner shell 80 and the larger internal chamber, a posterior fill channel 65 may be provided within the nose section near the posterior end, and an anterior fill channel 66 may be provided near the anterior end of the case. At the center of the posterior fill channel may be a boss 64, which may provide a binding surface around the threaded hole 62*a* and axial groove 63*a* of the posterior end 41.

Figure 9:
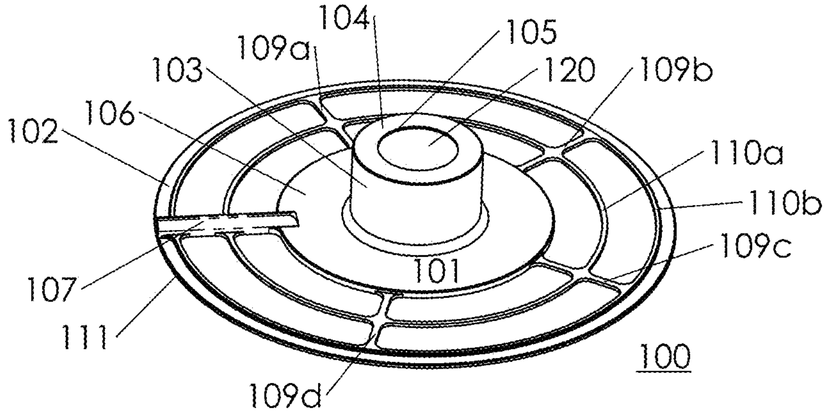
FIG. 9 is a perspective view of the header assembly according to an exemplary embodiment, oriented toward the tubular section of the header.
Figure 10:
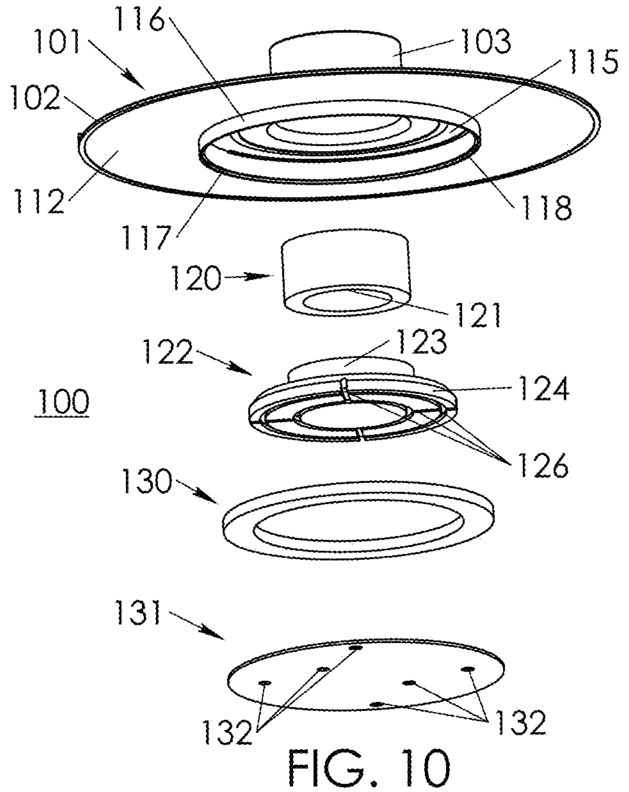
FIG. 10 is an exploded view of the header assembly according to an exemplary embodiment, oriented toward the skirt.
Figure 11:
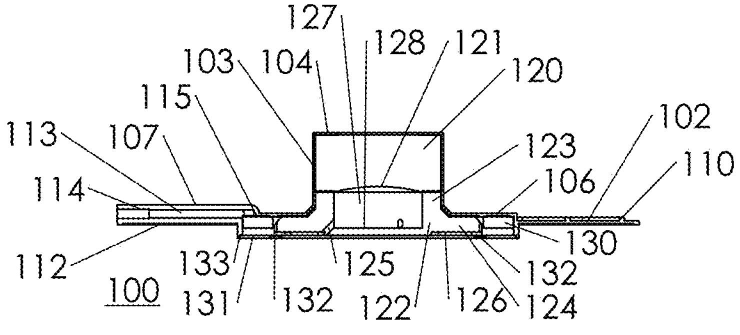
FIG. 11 is a cross-sectional view of the header assembly according to an exemplary embodiment, sectioned along the radial protrusion and radial passage.

Referring to FIGS. 9-11, an exemplary embodiment of a header assembly 100 is illustrated. The header 101 may include a wide flange portion 102 at its base with outer diameter 111, a hollow annular boss 106 extending slightly above the surface of flange portion 102, and an elongated tubular portion 103 terminating distally in a thin end terminal wall 104, which may define an opening 105 for needle access. Additionally, header 101 may include a radial protrusion 107 integrally formed with the flange portion 102, extending radially outward from the annular boss 106 toward the outer periphery of the flange. The radial protrusion 107 may define a radial passage 113, which may facilitate fluid communication from within the hollow annular boss 106 through the outer boundary of the header 101.

The flange portion 102 of header 101 may further include integral reinforcing ribs to enhance structural rigidity. These reinforcing ribs may include radial stiffening ribs 109*a*-109*d*, which extend radially outward from a central region, and annular stiffening ribs 110*a*-110*b*, which are concentrically disposed around the central region. The reinforcing ribs may exhibit increased thickness compared to the surrounding regions of the flange portion 102, thereby significantly enhancing the structural integrity and rigidity of header 101. Notably, given that this invention will be located within the human head, it is exposed to direct traumatic forces—both purposeful (ie. headstands with yoga, etc) and non-purposeful (ie. head trauma from car accidents, falls, etc)—and so structural integrity and maintaining strength comparable to a human skull may be understood to be an important attribute of some embodiments.

On the underside of header 101, as shown in FIG. 10, a tubular skirt 116 may extend downwardly from the flange portion 102, forming a circular enclosure sidewall. The tubular skirt 116 may further include an annular weld seat 117, defined by a circumferential counterbore extending partially into the thickness of the sidewall. The annular weld seat 117 may receive and seat a retention plate 131, providing an interface designed for secure welding attachment.

As best seen in the section view of FIG. 11, in some embodiments, header 101 may be configured to be of minimal wall thickness of approximately 0.2-0.3 mm nominally, yet manufacturable on account of stiffening members and tubular geometry. Undercut 112 may be provided beneath flange portion 102 to reduce material and provide clearance with the bellows assembly that will later be joined to it in the context of the full reservoir assembly.

Within the internal cavity of header 101, defined collectively by tubular portion 103, hollow annular boss 106, and tubular skirt 116, internal components may be accommodated as illustrated in, for example, the exploded view of FIG. 10 and the cross-sectional view of FIG. 11. These internal components may include septum 120, septum support insert 122, filter 130, and retention plate 131, all positioned and securely housed within the header 101.

According to the exemplary embodiment, the septum 120 may be a disk-shaped component molded from a tear-resistant elastomeric material, for example, a silicone elastomer with an approximate hardness of 30 Shore A. The septum 120 may allow for repeated needle penetration while maintaining a reliable seal. The septum may, in an exemplary embodiment, measure approximately 12 mm in diameter and 5 mm in thickness, and include a concave depression 121 on its internal face to prevent the compressed silicone from squeezing out below and blocking the needle tip. The septum 120 may be seated within the inner diameter bore of the tubular portion 103 of the header 101, where it may be held in place by a nominal diametral compression of approximately 5% to ensure self-sealing of the septum when the needle is removed and a fluid-tight seal between the septum's outer diameter and the inner diameter of the tubular portion 103. According to an exemplary embodiment, nominally there may be no axial compression up to a worst case of around 2% to avoid excessive stress against the retention plate 131, which may act to maintain the elevated position of the septum 120.

This configuration may allow for intermittent drug filling using a non-coring fill needle (for example, 24 gauge) without compromising the septum's sealing capability or structural integrity. It may be understood that some of the neurological medicines being injected into this invention accompany low or high ph attributes, that if leaked outside of the septum, could cause damaging brain injuries within multiple layers of the scalp and brain. The septum's thickness and elasticity may allow it to be pierced and resealed repeatedly while effectively resisting operational pressures. Once installed in the header 101, the effective orifice for needle penetration may be approximately 7 mm in diameter, ensuring ease of access while preserving the septum's leak-proof performance. Additionally, the configuration may be designed to accommodate needle insertion at an angle offset from the longitudinal axis of the inlet orifice by 15% or more.

Underneath the septum 120 there may be a septum support insert 122 that holds the septum 120 in position and establishes a needle fill cavity 127 for drug filling through a fill needle. The septum support insert 122 may occupy a portion of the tubular portion 103 of header 101, as well as a portion of the annular space defined between annular boss 106 and retention plate 131. The septum support insert 122 may be dimensioned to fit concentrically within the header 101 and abut the underside of the septum 120, thereby ensuring the septum remains securely positioned against the internal surface of the terminal wall 104 of the header. The septum support insert 122 may comprise a tubular portion 123, which defines an internal needle-fill cavity 127, and a flange portion 124 configured to occupy the internal volume within ID of filter 130 corresponding to the annular boss 106 and tubular skirt 116 axial boundaries within header 101.

When secured by retention plate 131, the septum support insert 122 may firmly retain the septum 120 against the terminal wall 104 of header 101 and provide a needle-stop surface 128. This needle-stop surface may limit the penetration depth of a needle inserted through the septum 120 into the needle-fill cavity 127. The plastic insert may be, for example, PEEK and/or titanium, and may comprise a needle stop surface that is sufficiently soft or strong not to damage the needle when abutted against. The needle fill cavity 127 may provide about 3 mm of axial clearance.

As best illustrated in the cross-sectional view of FIG. 11, the septum support insert 122 may further comprise a plurality of angled fluid communication passages 125 extending obliquely through its tubular portion 123, facilitating fluid flow between the needle-fill cavity 127 and the underside surface of the flange portion 124. The needle stop surface 128 may remain uninterrupted by any passage openings to preserve its structural integrity and functionality. Additionally, the underside of flange portion 124 may include an integrated flow-channel network 126, including radial and annular flow channels that distribute fluid received from the angled passages 125 that intersect the sidewall of the needle-fill cavity 127.

The filter 130, according to an exemplary embodiment, may be an annular, ring-shaped sintered titanium filter positioned within the annular space defined radially between the septum support insert 122 and the tubular skirt 116 of the header 101 and axially constrained between the annular boss portion 106 of the header and the retention plate 131. The sintered titanium filter 130 may be secured to the header 101 by fillet welds at both its inner diameter (ID) and outer diameter (OD) interfaces, creating robust, sealed connections between the filter 130 and the header 101.

Sintered titanium filters may be porous filtration elements produced by compressing and sintering fine titanium powder at temperatures below its melting point, resulting in a rigid structure with uniform pore size. This manufacturing method may yield filters with several advantages over polymer-based alternatives. Sintered titanium offers exceptional corrosion resistance, making it suitable for harsh chemical environments such as acids, chlorides, etc. It exhibits high thermal stability, maintaining integrity at temperatures exceeding 500° C., which is ideal for processes involving heat, including autoclave sterilization. This attribute may be important in some embodiments, since in the operating room, the device being dropped or contaminated during the implantation process may be prevented, and so in this emergency situation, it may be understood to be possible to sterilize and autoclave while the patient remains anesthetized, so that the expensive device does not have to be discarded. Notably, other common skull implant materials like porous polyethylene or PMMA, may melt inside a high temperature autoclaver and therefore require the surgeon to use a second device instead. Its mechanical strength allows it to withstand high pressure differentials without deformation, and its biocompatibility makes it appropriate for medical applications. Their inert, non-shedding nature eliminates the risk of media migration or contamination. Notably, sintered titanium filters typically have a lower bubble point than polymeric membrane filters of equivalent nominal pore size, due to titanium's lower surface energy, which reduces liquid retention. Another key advantage is weldability; sintered titanium filters can be welded directly to a header, eliminating the need for gaskets and ensuring a leak-proof seal.

In the exemplary embodiment, the filter 130 may have a pore size of less than 0.2 micrometers, enabling it to block particulates and bacteria from reaching the downstream components and the brain. For the embodiment including regulator chips featuring microchannels, it may be especially critical to implement robust upstream filtering.

The fillet welds at the ID and OD interfaces may form fluid-tight seals configured to prevent fluid bypass around the filter 130, thereby ensuring that all fluid flowing through the annular region is constrained to pass exclusively through the porous structure of the sintered titanium filter 130.

As best illustrated in FIG. 11, an annular groove 115 of the header 101 may be strategically positioned to define a flow channel in fluid communication with the radial passage 113. Additionally, a radial counterbore 114 may be provided at the outer end of the radial passage 113, configured for interfacing with an outlet tube, as described further below in reference to the complete reservoir assembly.

Retention plate 131 may be configured to support the septum support insert 122, and consequently, the septum 120. The retention plate 131 may be a thin, planar titanium element fabricated by, for example, laser cutting or die cutting. The retention plate 131 may include a plurality of distributed fluid communication holes 132 that facilitate fluid transfer between the internal cavity of the header 101 and the underlying drug reservoir. The retention plate 131 may be seated within the annular weld seat 117 of the tubular skirt 116 up against the mechanical stop surface 118 and structurally affixed thereto by a circumferential laser weld formed along the peripheral seam 133.

As further illustrated and clarified in subsequent figures describing embodiments of the reservoir assembly, the distal end of the tubular skirt 116 may provide a mechanical stop surface to establish an end-of-travel limit position for an internal bellows mechanism. This limit position may correspond to the fully compressed state of the bellows, indicating complete expulsion of drug fluid from the reservoir.

Figure 12:
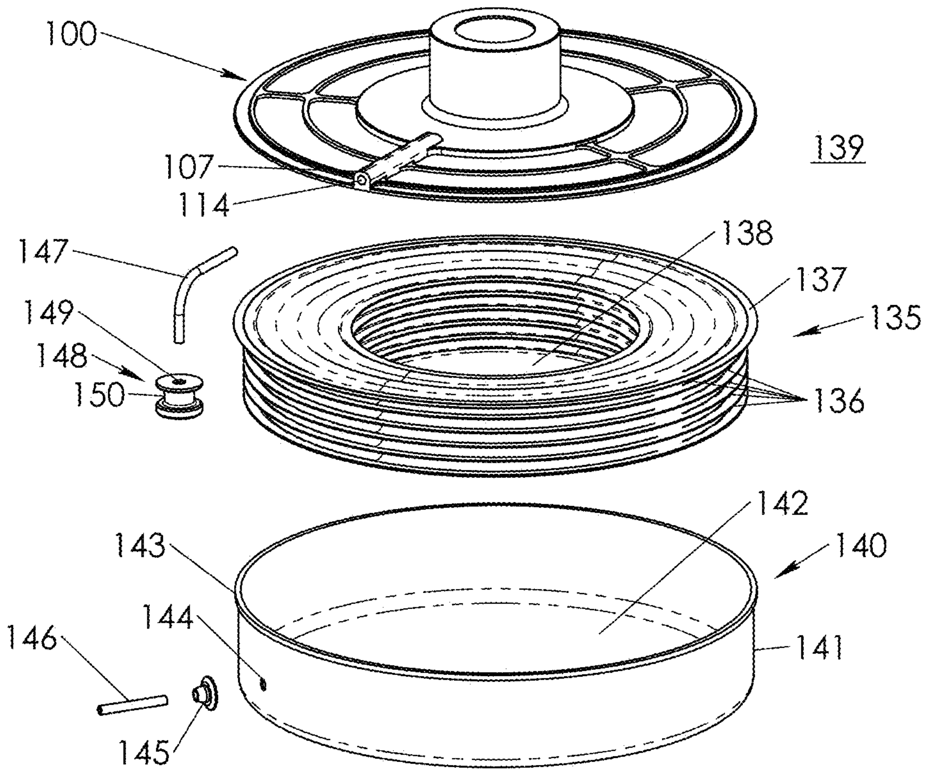
FIG. 12 is an exploded view of the reservoir assembly according to an exemplary embodiment, oriented toward the interior of the can.
Figure 13:
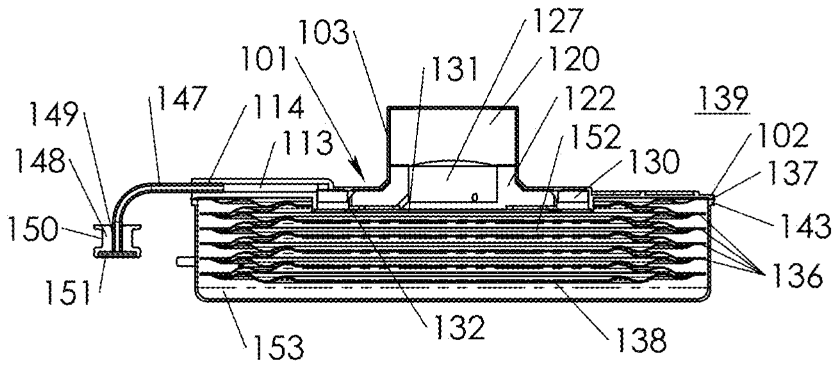
FIG. 13 is a sectional view of the reservoir assembly according to an exemplary embodiment, taken along the mid-plane of the outlet tube and plug adapter.

Referring to FIGS. 12-13, the reservoir assembly 139 may include three primary components: a bellows assembly 135, a header assembly 100, and a can component 140. According to an exemplary embodiment, the bellows assembly 135 may be hermetically welded in a triple-weld with the header assembly 100 and the can component 140, thereby creating an enclosed drug reservoir 152, as shown in FIG. 13, and defining an isolated propellant chamber 153 that acts against the exterior of bellows 135. Integration of these three components may establish a hermetically-sealed weld joint and propellant chamber, enabling controlled drug delivery through the compression of the bellows assembly 135 in response to the fluid volume of drug reservoir 152.

The metal bellows assembly 135 may be a precisely engineered, flexible, and hermetically sealed mechanical component constructed from thin-walled metal sheet (foil) that is formed into a series of convolutions resembling accordion-like folds. This structure may expand and contract axially while maintaining a hermetic seal, thereby enabling it to accommodate variations in pressure, volume, or axial displacement within the system. In the case of edge-welded metal bellows, each convolution may be welded at both its inner and outer edges. The performance characteristics of the bellows (including its spring rate, fatigue life, and pressure capacity) may be determined by the number of convolutions, their geometric profile, and/or the wall thickness of the material.

According to the exemplary embodiment, the bellows may be fabricated from 0.051 mm-thick sheets and feature a ripple geometry optimized for tight nesting when the bellows assembly 135 is fully compressed, thereby maximizing volumetric efficiency while preserving mechanical compliance and durability.

Bellows assembly 135 may include a series of convolutions 136 characterized by alternating inner diameter (ID) and outer diameter (OD) weld interfaces, wherein the ID and OD dimensions of each intermediate convolution remain substantially consistent along the length of the bellows. At its open terminal end, the bellows assembly 135 may include an enlarged outer diameter terminal flange 137 that provides a weld interface between the header flange 102 and the weld flange 143 of the can component 140. At its closed terminal end, the bellows assembly 135 may be sealed by a welded terminal plate 138. Both the terminal flange 137 and the closed terminal plate 138 may exhibit convolution geometries substantially identical to those of the intermediate convolutions 136. Each convolution may include three ripples, allowing adjacent convolutions to nest closely within each other when the bellows assembly 135 is fully compressed. In other embodiments, a different number of ripples may be included.

According to the exemplary embodiment, there are nine convolutions 136 between the terminal plate 138 and terminal flange 137, which may accommodate a range of motion of the terminal plate 138 of about 7.5 mm, for example, going from a compressed length of 1.5 mm to an expanded length of 9 mm. The thin wall, ripple geometry, and width of convolutions 136 may contribute to minimizing the axial stiffness of the bellows assembly 135, which in turn may contribute to minimizing the operating pressure of the system, allowing a low vapor pressure propellant to be used.

The can component 140 may include a tubular body 141 having a closed end 142, defining an enclosure adapted to receive the bellows assembly 135 and establish the external boundary of the propellant chamber. The radial sidewall of tubular body 141 and the axial wall at its closed end 142 may exhibit a minimal wall thickness—for example, approximately 0.2 mm—which may reduce the overall titanium volume. It may be understood reduction of overall titanium volume may assist in minimizing radiographic artifact and preventing obstruction of imaging required to detect life-saving situations, like possible brain tumor recurrence underneath for example. At its open end, the can component 140 may include an integrally formed, thicker weld flange 143, designed to provide structural reinforcement and to facilitate secure and robust welding interfaces with both the bellows assembly 135 and the header assembly 100.

The reservoir assembly 139 may be welded together along the seam where the bellows terminal flange 137 is sandwiched between the can 140 and the header assembly 100, resulting in all three components being joined in a single operational step. The weld may be performed using laser welding due to its precision and minimal heat-affected zone, or TIG welding may also be employed as an alternative. In other embodiments, other forms of welding or joining may be utilized. At the weld joint, in an exemplary embodiment, the can 140 may feature a weld flange 143 having a locally thickened radial wall of approximately 0.5 mm, providing reinforcement and weld robustness, in contrast to the 0.2-0.3 mm wall thickness found throughout most of the can body.

In some embodiments, the drug delivery system may incorporate a compact reservoir assembly 139 architecture in which both the septum 120 (for refill access) and the filter 130 are coaxially integrated within the cylindrical envelope defined by the header assembly 100, the can 140, and the bellows assembly 135. This coaxial configuration may minimize the spatial footprint of the reservoir subsystem, eliminating the need for offset auxiliary components and enabling a more efficient and compact system integration.

The reservoir assembly 139 may be designed to hold approximately 8 cc of drug while minimizing fluid dead volume, which may be defined as the residual fluid that remains when the bellows are fully distended against the end stop established by the header. In an exemplary embodiment, the outer diameter of the can 140 may be approximately 45 mm, and the bellows terminal plate 138 may travel approximately 7.5 mm from the bottom of the can 140 to the tubular skirt 116 of the header 101.

In reference to FIG. 13, the axial length of the tubular portion 103 of the header 101, which is occupied by the septum 120, septum support insert 122, and header retention plate 131, may be understood to contribute to the overall height of the reservoir assembly 139. According to an exemplary embodiment, this total height may be approximately 17.5 mm, encompassing all internal components necessary to support the filling and sealing functions of the drug reservoir system. A therapeutic agent injected into the needle fill cavity 127 may be in fluid communication with the drug reservoir 152 inside the bellows 135. The therapeutic agent within the drug reservoir 152 may also be in fluid communication with radial passage 113, providing a fluid passage to an outlet tube 147. Proper fluid communication, absent of any leaks, may be understood to increase safety of the device.

To facilitate propellant filling, the can component 140 may include an aperture 144 positioned in the sidewall of the tubular portion 141. A flange adapter 145, may be pre-welded to a fill tube 146, and may be sealingly-affixed via welding to the external surface of the can 140, circumferentially surrounding aperture 144. This configuration may create a hermetic interface, enabling secure fluid communication between an external propellant source and the internal propellant chamber 153, with propellant introduced through the attached fill tube 146.

Once the header assembly is completed, the propellant may be charged into the propellant chamber through the fill tube 146, which may be initially manufactured with excess length to allow for multiple charging attempts, enabling precise control over the mass of propellant introduced. It may be understood that this configuration may ensure that, when the bellows is fully compressed, nearly no propellant remains in the liquid phase. This approach may therefore minimize the internal pressure exerted on the system during subsequent exposure to elevated temperatures and pressures associated with, for example, manufacturing steps and autoclave sterilization.

After the target charge mass is confirmed to be within acceptable limits, the fill tube 146 may be crimped near the outer diameter of the can 140, and the crimped section may be subsequently welded. This process establishes a fully hermetically sealed propellant chamber, ensuring long-term containment and stability of the propellant under operational and environmental stresses.

According to an exemplary embodiment, a propellant-driven bellows drug pump may utilize an internal propellant to maintain a pressurized bellows mechanism, enabling controlled drug delivery. The system may integrate an expandable bellows assembly 135 filled with a therapeutic agent, where the bellows serves as a dynamic reservoir capable of expanding and contracting. One side of the bellows may be connected to the drug reservoir 152, while the opposing side may be the propellant chamber 153 exposed to the pressurized propellant. Since the propellant contained within the propellant chamber 153 between the bellows assembly 135 and the can 140 can be in both liquid and vapor phases, the system may remain relatively insensitive to the volume of drug within the reservoir, contributing to a low variability of pressure in the drug reservoir 152.

When the bellows reservoir in a propellant-driven, drug delivery device is filled with the drug, a sequence of thermodynamic events may occur to regulate and maintain consistent pressure. Initially, as the drug fills the reservoir to capacity, the bellows may expand, reducing the available volume in the adjacent propellant chamber. This reduction in space may cause the pressure within the propellant chamber to rise above the equilibrium vapor pressure of the propellant, triggering condensation of the gaseous propellant back into its liquid phase. As this phase transition occurs, the gas volume may decrease, stabilizing the internal pressure at the equilibrium level while the bellows remains fully expanded.

At this stage, the propellant may predominantly exist in liquid form and exert a constant external pressure on the drug-filled bellows, preparing the system for operation. During drug dispensing, the bellows may then be compressed by the pressure exerted by the evaporating propellant, which may drive the drug out of the reservoir. As the drug is expelled and the bellows contract, the volume of the propellant chamber increases, which may allow a portion of the liquid propellant to re-evaporate, thereby maintaining the chamber pressure.

This cycle of evaporation and condensation may continue throughout the operation of the pump. The propellant may undergo continuous micro-phase transitions that self-regulate the pressure applied to the bellows, ensuring a consistent delivery force. This mechanism may thereby enable a steady, controlled release of the drug, making the system ideal for long-term, precise drug administration in compact or implantable devices. Importantly, brain medicine quantities and flow rates are a known essential attribute of convection-enhanced delivery, therefore in some embodiments highly accurate drug delivery may be required—for when flow is too high, overdose sequelae and/or brain injury may occur, versus when flow is to low, the medicine may lose its efficacy and inability to treat chronic brain disease.

The pressure applied may depend on the thermodynamic properties of the selected propellant, which may be chosen for its stable vapor pressure characteristics—for example, a fluorocarbon or other low-boiling-point liquid. Fluorocarbons may be particularly well-suited for some applications due to their predictable and temperature-stable vapor pressure profiles.

In some embodiments, the propellant may be selected to exhibit as low a vapor pressure as possible while still generating sufficient force to compress the bellows assembly 135, overcome downstream resistance, and/or provide an acceptable inlet pressure range to the downstream flow regulator chips 158 (described in reference to FIGS. 14-19). Flow regulator chips 158 may modulate the outflow to achieve a near-constant drug outflow rate to each of the catheter fittings 190. The propellant-driven reservoir assembly 139 may operate in conjunction with the flow regulator chips 158 of the regulator assembly 155 to ensure a near-uniform drug delivery rate throughout the duration of the device operation. This phase-change-driven mechanism may be understood to offer dual advantages of compactness and mechanical simplicity while enabling precise and reliable micro-dosing over extended periods.

In accordance with an exemplary system design, which may minimize the operating pressure of the reservoir, the selected propellant may be characterized by a relatively low vapor pressure-yet may be sufficient to drive bellows displacement and overcome the impedance of the downstream flow regulator chips 158. This displacement may overcome the inherent stiffness of the bellows assembly 135, the downstream pressure within the system, and ensure that the regulator chips 158 receive an acceptable range of inlet pressures. It may thereby maintain a nearly constant outflow rate at each of the two catheter fittings 190 across the full range of operating conditions.

In an exemplary embodiment of the system, the propellant may exhibit a vapor pressure of 1850 mBar±300 within an operating temperature range of 38.5° C.±2.5° C. A suitable propellant may be, for example, R-1233zd (Trans-1-chloro-3,3,3-trifluoropropene), which may be understood to meet the pressure and thermal stability requirements of the design. Alternative options may include, for example, but not limited to, R-11 or other engineered propellant blends that provide comparable performance characteristics.

Figure 20:
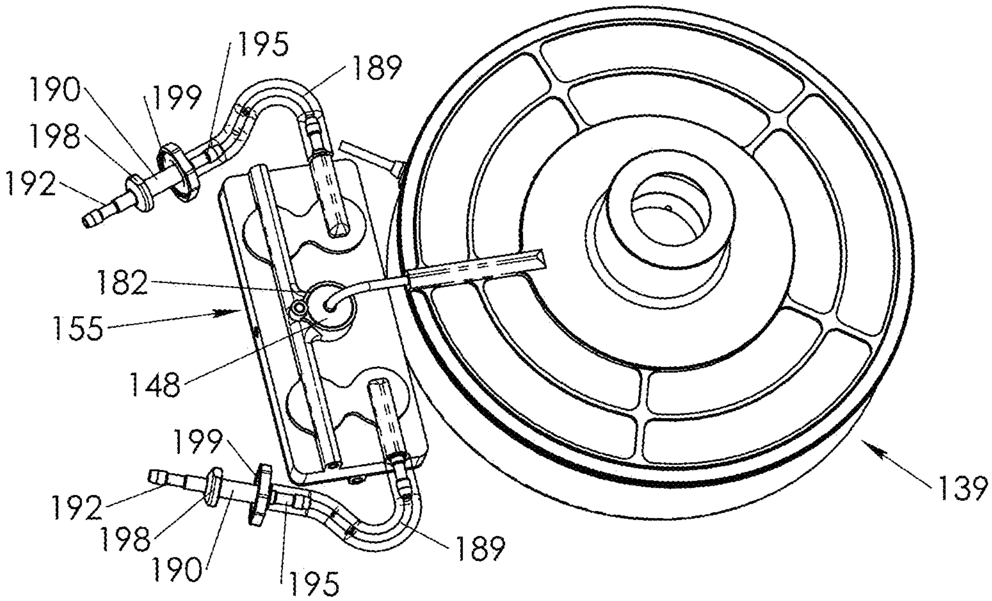
FIG. 20 is a perspective view of the drug delivery system according to an exemplary embodiment, oriented toward the plug and socket interface between the reservoir and regulator assemblies.
Figure 21:
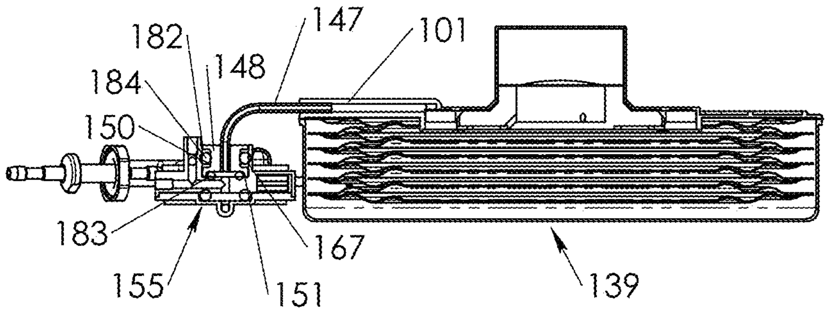
FIG. 21 is a sectional view of an exemplary embodiment, taken along the mid-plane of the reservoir and flow regulator assemblies.

The reservoir outlet tube 147 may be a small titanium tube segment hermetically welded to the radial protrusion 107 of the header assembly 100, establishing fluid communication between the internal drug reservoir 152 and downstream components of the drug delivery system. The outlet tube 147 may include an integrally formed bend, which may redirect fluid outflow toward an off-axis auxiliary position adjacent to and oriented substantially parallel to the exterior surface of the can component 140. This configuration may facilitate optimal connection and streamlined routing of fluid to the regulator assembly 155, as illustrated in FIGS. 20-21.

Referring again to FIGS. 12-13, the outlet tube 147 may be sealingly-affixed by, for example welding, at an annular weld seam located at the interface between the outer diameter (OD) of the outlet tube 147 and a radial counterbore 114 formed within the radial protrusion 107 of the header assembly 100, where the outlet tube 147 is concentrically seated within the radial counterbore 114. The weld seam may thereby provide a hermetic, fluid-tight connection. As shown in FIG. 13, the axial position of the outlet tube 147 within the radial protrusion 107 may be precisely determined by an end face of the radial counterbore 114, which may serve as a mechanical stop against which the outlet tube 147 is seated. This arrangement ensures consistent axial positioning of the outlet tube 147 during assembly and welding, thereby maintaining proper alignment and fluid communication between the drug reservoir 152 and downstream drug delivery system components.

A plug adapter 148 may be sealingly-welded at the downstream axial end of the outlet tube 147. The plug adapter 148 may include an axial lumen 149 dimensioned to concentrically receive the outlet tube 147. The weld interface between the plug adapter 148 and the outlet tube 147 may be formed at the axial end face of the outlet tube, specifically at the junction between the outer diameter (OD) of the outlet tube 147 and the inner diameter (ID) of the adapter lumen 149, which may create a robust, hermetic, and fluid-tight connection.

The plug adapter 148 may have a releasable connection with a corresponding socket interface of the flow regulator assembly 155 (described in reference to FIGS. 14-19). The plug adapter 148 may include an external radial O-ring groove 150 dimensioned to accommodate a radial sealing O-ring, as well as a distal-end axial counterbore 151 adapted to seat an axial sealing O-ring. These sealing elements may collectively provide dual-sealing functionality—both radial and axial—thereby ensuring a secure, leak-tight interface between the plug adapter 148 and the socket interface of the flow regulator assembly 155. Further specific details regarding the sealing interface and associated functional characteristics are described with reference to FIGS. 21-22.

Referring now to FIGS. 14-19, a regulator assembly 155, according to the exemplary embodiment, is described in detail. Regulator assembly 155 may be compact and may fit within the thinner posterior region of the case 40 (best seen in later reference to FIG. 22). According to an exemplary embodiment, the regulator assembly 155 may include a two-part titanium enclosure made of a manifold housing 156 and lid housing 157, which may be sealingly-joined together—for example by laser welding—along a mating seam 181. The welded joint may form a complete, sealed enclosure and establish the internal fluid pathways necessary for the operation of the regulator assembly 155. In some embodiments, titanium may be particularly advantageous, as it may allow for secure, precision welding using a very small joint, enabling wall thicknesses to be minimized and the overall structure to remain compact. Additionally, the total titanium mass of the regulator enclosure may represent only a small fraction of the case volume, resulting in minimal MRI artifact from these fluidic components. Again, minimal MRI artifact may be understood to increase long-term safety of each neurosurgical patient post-implantation, as a way to assure proper imaging and disease surveillance.

Figure 14:
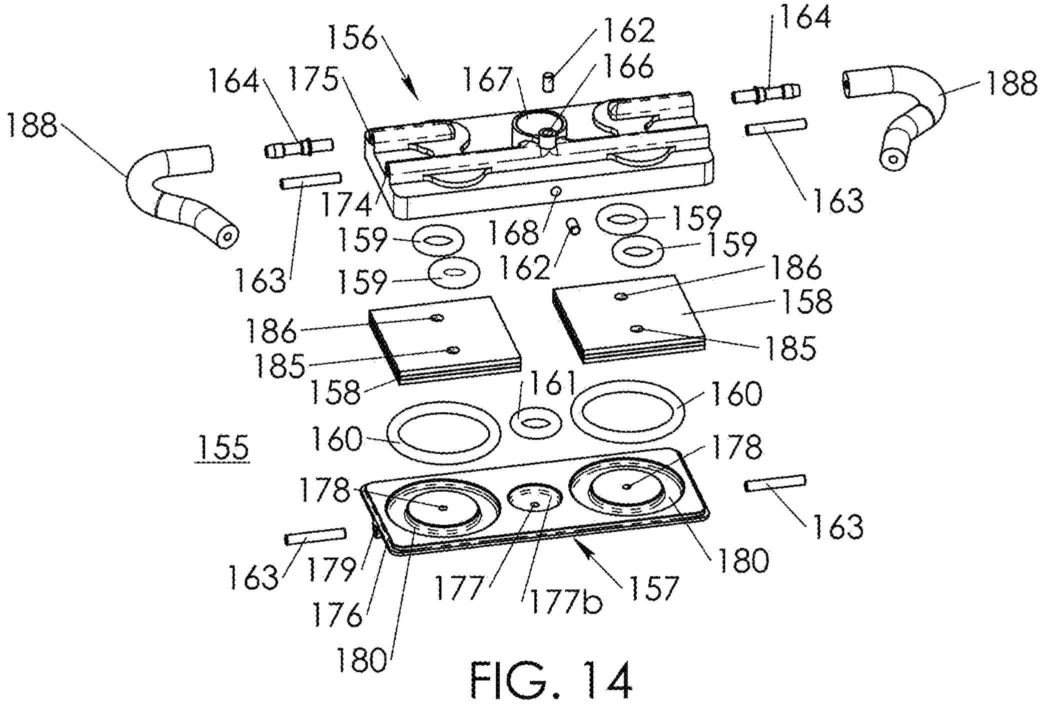
FIG. 14 is an exploded view of the regulator assembly according to an exemplary embodiment, oriented toward the manifold housing.
Figure 15:
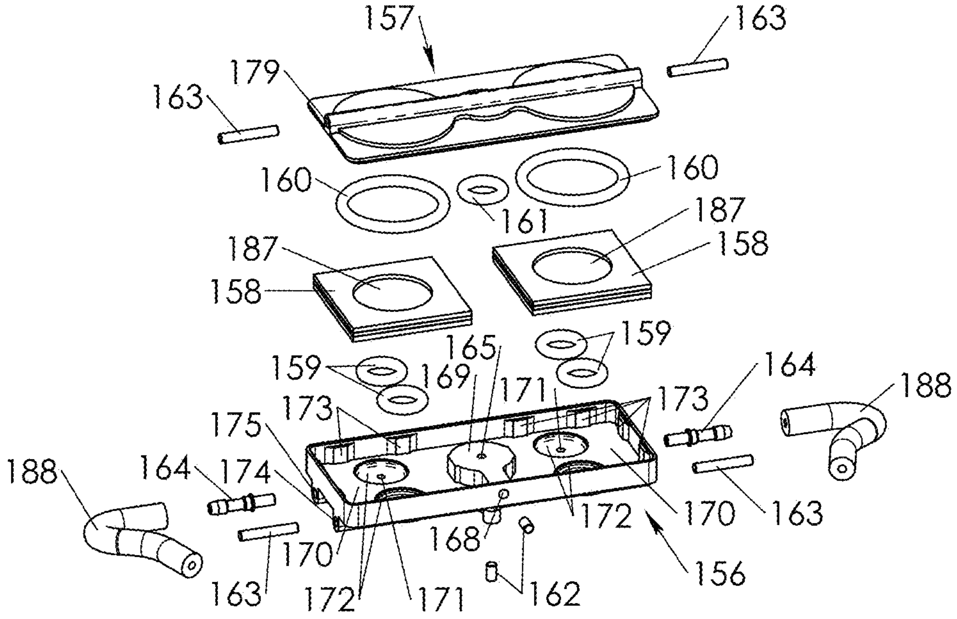
FIG. 15 is an exploded view of the regulator assembly according to an exemplary embodiment, oriented toward the lid housing.
Figure 16:
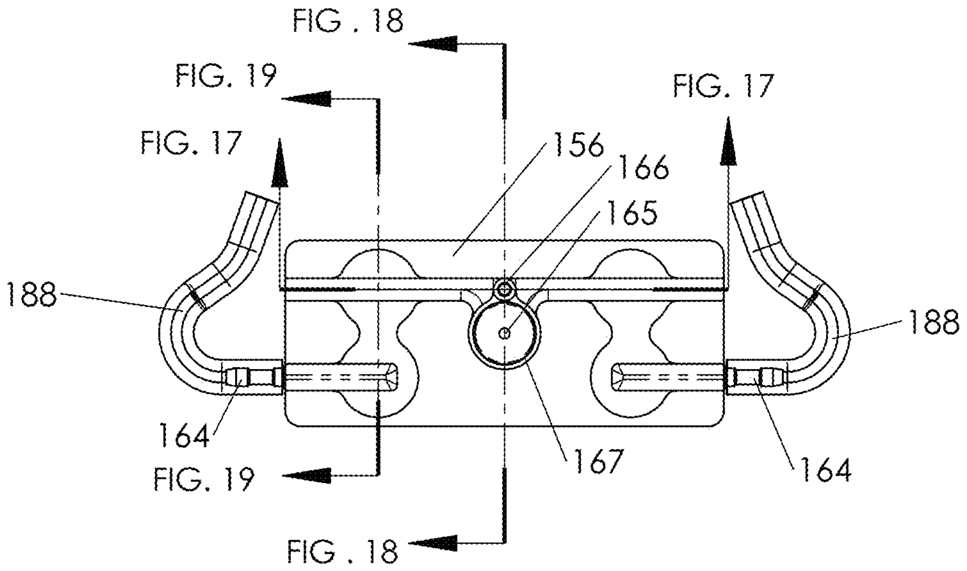
FIG. 16 is an orthogonal view of the regulator assembly according to an exemplary embodiment, oriented toward the manifold housing.

As shown particularly in the exploded views of FIGS. 14-15, the regulator assembly 155 may include one or more of the following components: a manifold housing 156, a lid housing 157, two MEMS flow regulator chips 158, four port O-rings 159, two diaphragm O-rings 160, one inter-housing O-ring 161, two short plugs 162, four long plugs 163, two outlet fittings 164, and/or two flexible tubes 188.

Each flow regulator chip 158 may be housed within a compact, rectangular envelope, which in an exemplary embodiment may be approximately 11 mm by 11 mm by 1.3 mm. Each regulator chip 158 may include an inlet port 185, an adjacent outlet port 186 positioned on a first major face, and/or a larger diaphragm port 187 located on the opposing second major face. The diaphragm port 187 may apply a reference inlet pressure to an internal diaphragm mechanism housed within the regulator chip 158, thereby facilitating precise flow regulation.

In an exemplary embodiment, the regulator chip 158 may be a MEMS-based fluidic device designed to deliver a constant outflow rate over a range of inlet pressures, operating passively without active feedback. U.S. Pat. Nos. 8,539,981 and 8,790,318 are herein incorporated by reference as describing the exemplary structure and functionality of regulator chip 158. The microelectromechanical systems (MEMS) devices may be fabricated using techniques derived from integrated circuit (IC) manufacturing, with additional processes tailored for creating mechanical structures at the microscale. The MEMS flow regulator may be fabricated from, for example, a silicon or a silicon-borosilicate composite. The fabrication process may involve multiple steps carried out on a silicon wafer. The regulator chip 158 may rely on an integrated flexible diaphragm that regulates the number of open microchannels as a function of the pressure differential between a variable inlet pressure and a relatively constant outlet pressure. The MEMS flow regulator may maintain a substantially constant drug flow rate between, for example, approximately 0.5 to 10 microliters per minute over a differential pressure range of 3-30 psi. The flow rate and pressure range may be different in other embodiments and for other applications.

The regulator chip 158 may maintain a near-constant flow rate by dynamically adjusting flow resistance based on the pressure differential between the inlet (reference) and outlet. The inlet pressure may be communicated to one side of a flexible diaphragm, while the outlet pressure may act on the opposing side. As the pressure differential increases, the diaphragm may deflect to progressively seal microchannels, increasing flow resistance. This progressive reduction in flow paths may be understood to increase the total hydraulic resistance, which may compensate for the higher driving pressure. When the pressure drop is smaller, the diaphragm may relax, allowing more channels to open and thereby reducing resistance. This dynamic behavior may passively regulate flow rate, keeping it relatively constant across a range of output pressures and flow demands. This mechanism may thereby ensure pressure-adaptive, flow stabilization using no active control elements.

The first half of the regulator housing, the manifold housing 156, may include an integrated flow circuit adapted to distribute fluid inlet pressure to the inlet ports 185 of the pressure regulator chips 158, and to route fluid from the corresponding outlet ports 186 to respective outlet fittings 164 mounted externally on side surfaces of the manifold housing 156. The second half, the lid housing 157, may enclose the manifold housing 156 and define internal fluid pathways configured to route inlet reference pressure to the diaphragm ports 187 of the regulator chips 158.

The manifold housing 156 may include a larger internal cavity incorporating chip-receiving cavities 170 positioned on opposite sides of a central boss 169. Each chip-receiving cavity 170 may constrain and precisely locate each of the regulator chips 158 within the manifold housing 156. The central boss 169, positioned between the chip-receiving cavities 170, may further include internal flow passages, including a coaxial hole 165, which may deliver a reference pressure to the lid housing 157, placing it in fluid communication with the diaphragm ports 187 of the regulator chips 158.

Lateral movement of each of the regulator chips 158 within the manifold housing 156 may be constrained by raised locating ribs 173, integrally formed on the internal surfaces of the manifold housing side walls. The locating ribs 173 may extend inwardly relative to the nominal side wall thickness, thereby providing precise lateral positioning and structural support for each of the regulator chips 158 within the respective chip-receiving cavities 170.

Corresponding to the locations of each flow port on the regulator chips 158, the manifold housing 156 may incorporate coaxially-aligned, blind holes 171 with the adjacent counterbores 172 configured to seat the corresponding O-rings 159. Each of the O-rings 159 may sealingly engage the respective face of the regulator chips 158, thereby establishing a secure, fluid-tight seal around each port interface.

A socket 167, provided within manifold housing 156, may sealingly receive the plug adapter 148 of reservoir assembly 139 (as best seen in later reference to FIG. 22). The manifold housing 156 may further incorporate internal fluid-routing features to redirect fluid flow from the socket interface 176 into internal pathways oriented orthogonally with respect to the external surfaces of the manifold housing 156. Specifically, these fluid pathways may extend along axes parallel to both the short and long dimensions of the manifold housing 156, facilitating precise and compact fluid routing within the internal volume of the manifold housing.

The internal fluid-routing features according to an exemplary embodiment of the manifold housing 156 will now be described sequentially, proceeding from the upstream inlet socket 167 toward the downstream outlet ports 175. Beneath the inlet socket 167, the manifold housing 156 may include a coaxial hole 165 that forms an internal passage, enabling reference pressure to pass through to the lid housing 157. The coaxial hole 165 may further intersect a perpendicular blind side hole 168 positioned centrally within the manifold housing 156, creating a pathway directed toward the plane shared by both axes of the inlet ports 185 of the regulator chips 158. The perpendicular blind side hole 168 may extend parallel to the short axis of manifold housing 156, oriented orthogonally relative to the inlet socket 167 axis, thereby providing a transverse fluid communication pathway within the manifold housing.

Within the manifold housing 157, an adjacent axial blind hole 166 may extend parallel to the inlet socket 167 and intersect with the perpendicular blind side hole 168, thereby establishing a redirected internal fluid pathway. The axial blind hole 166 may run adjacent to and in alignment with the inlet socket 167, serving to route fluid toward the manifold-facing side of the manifold housing 156.

Both the perpendicular side hole 168 and the axial blind hole 166 may terminate in openings at the external surface of the manifold housing 156. These external openings may be sealed using respective short plugs 162, each of which may be a cylindrical pin with a diameter approximately matching that of its corresponding hole. The short plugs 162 may be hermetically sealed to the manifold housing 156 via, for example, laser welding, ensuring secure closure and preventing fluid leakage at each plug site.

The manifold housing 156 may further include an inlet cross-hole 174, which may be a through-hole oriented along the long axis of the manifold housing 156 and positioned to intersect with the axes of the inlet ports 185 of each pressure regulator chip 158. The inlet cross-hole 174 may thereby divide the single fluid inlet supply into two separate flow circuits, facilitating independent fluid distribution to each respective regulator chip inlet port.

The open ends of the inlet cross-hole 174, which may extend along the entire length of the manifold housing 156, may be each sealed with a respective long plug 163. Each long plug 163 may be a cylindrical pin dimensioned with a diameter approximately equal to that of the inlet cross-hole (which may include a counterbore at each end) and may be sealingly-affixed by, for example, laser welding flush with the outer surfaces of the manifold housing 156, thereby establishing a hermetic seal.

Each long plug 163 may further extend axially inward within the counterbores of the inlet cross-hole 174 to terminate in close proximity to the internal blind port holes 171 in fluid communication with the inlet ports 185 of the flow regulator chips 158, effectively minimizing internal dead volume within the fluid flow pathways.

The manifold housing 156 may further include two outlet blind holes 175 positioned on opposing sides, oriented perpendicular to and in axial alignment with the outlet ports 186 of each flow regulator chip 158. The outlet blind holes 175 may be in fluid communication with corresponding blind port holes 171 aligned directly with the outlet ports 186 of the flow regulator chips 158.

An outlet fitting 164 may be received within each outlet blind hole 175. Each of the outlet fittings 164 may include an internal through-hole, a cylindrical interface portion extending to a flange at one end, and/or a barbed interface at the opposite end. The flange of each outlet fitting 164 may be sealingly-affixed by, for example, laser welding to the exterior side surfaces of the manifold housing 156, providing a secure and sealed attachment.

The barb interface of each outlet fitting 164 may be adapted for secure, fluid-tight engagement with a corresponding flexible tube 188. Each barb interface may feature an enlarged distal tip portion dimensioned slightly larger than the lumen diameter of the flexible tube 188, thereby establishing an interference fit that maintains a reliable, leak-resistant seal between the flexible tube 188 and the outlet fitting 164.

In some embodiments, due to the relatively lower fluid pressure downstream from the flow regulator chips 158 compared to the upstream pressure within the system, the downstream interfaces, including the barb fittings and flexible tube connections, may not require redundant or strictly hermetic-sealing configurations. Accordingly, simplified interference-fit seals or non-hermetic attachments may be sufficient to maintain reliable fluid-tight integrity under normal operating conditions.

The exterior surface of the manifold housing 156 may be selectively relieved, forming external bosses and elongated protrusions aligned along the long axis of the housing. These protrusions may correspond specifically to the locations of the inlet cross-hole 174 and the outlet blind holes 175, thereby maintaining a consistent minimal wall thickness of, for example, approximately 0.3 mm around all internal flow passages and cavities. This structural arrangement may optimize material usage to minimize titanium volume while ensuring structural integrity when pressurized.

Figure 17:
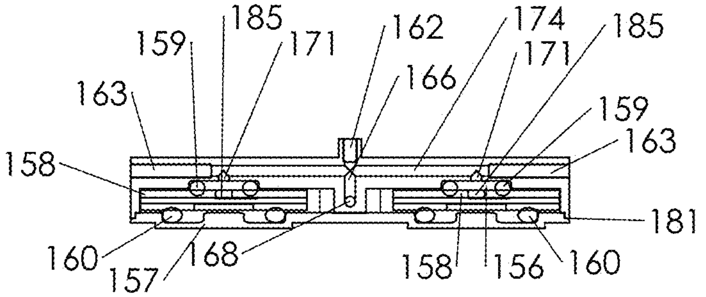
FIG. 17 is a sectional view of the regulator assembly, taken along the indicated section line of FIG. 16, dissecting the inlet cross hole along a plane parallel to the long axis of the regulator assembly.
Figure 18:
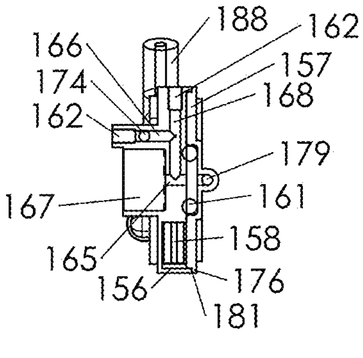
FIG. 18 is a sectional view of the regulator assembly, taken along the indicated section line of FIG. 16, dissecting the socket along a plane parallel to the short axis of the regulator assembly.
Figure 19:
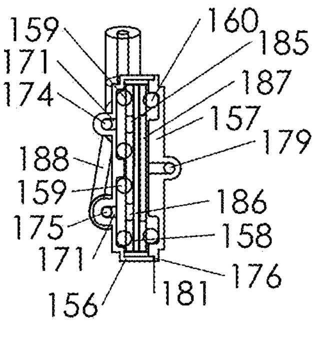
FIG. 19 is a sectional view of the regulator assembly, taken along the indicated section line of FIG. 16, dissecting one of the regulator chips along a plane parallel to the short axis.

The lid housing 157 may enclose manifold housing 156 and fully encase the regulator chips 158 within. The lid housing 157 may include a stepped peripheral lip 176 designed to achieve precise alignment and controlled fit-up with the corresponding mating surface of the manifold housing 156. The stepped peripheral lip 176 may further provide an optimal interface for laser welding along the peripheral seam 181 between the lid housing and the manifold housing, as seen in FIGS. 17-19, thereby ensuring a robust and hermetic joint between the two components.

The lid housing 157 may include a central pass-through hole 177, which may be in coaxial alignment with the coaxial hole 165 and the inlet socket 167 of the manifold housing 156. Additionally, the central region of the lid housing 157 may include a coaxially-aligned counterbore **177*b* around the pass-through hole 177, dimensioned for seating an inter-housing sealing O-ring 161. The seated inter-housing O-ring may thereby establish a reliable fluid-tight axial seal between the manifold housing 156 and the lid housing 157** at their mating interface.

The lid housing 157 also includes diaphragm blind holes 178 disposed in coaxial alignment with the diaphragm ports 187 of the flow regulator chips 158. Additionally, reference cross-hole 179 may extend longitudinally along the entire length of the lid housing 157, intersecting both diaphragm blind holes 178 and the central pass-through hole 177. The reference cross-hole 179 may thereby establish a continuous fluid communication pathway connecting the central pass-through hole 177 to each of the diaphragm blind holes 178. Consequently, this configuration may expose the diaphragm ports 187 of the flow regulator chips 158 directly to the inlet pressure of the fluid system, providing an accurate reference pressure for the operation of the regulator chips 158.

The external openings at both ends of the reference cross-hole 179 in the lid housing 157 may be each sealed by a respective long plug 163. Each of the long plugs 163 may be a cylindrical pin dimensioned approximately equal to the diameter of the end counterbores of the reference cross-hole and is seated flush against the end surfaces of the lid housing 157, being sealingly-affixed by, for example, laser welding. Additionally, each long plug 163 may extend inwardly within the reference cross-hole 179, terminating in close proximity to the diaphragm blind holes 178, thereby minimizing internal dead volume within the fluid pathway. It may be understood that minimizing dead volume may be important in some embodiments given that previously-injected medicine may become ineffective and potentially toxic (ie. due to temperature-sensitive degradation) when mixing with newly-injected medicine, and can therefore have severe consequences when dead volume is not minimized.

The lid housing 157 may further include two axial O-ring grooves 180, each concentrically-positioned relative to the diaphragm blind holes 178. The axial O-ring grooves 180 may be dimensioned to seat the diaphragm O-rings 160, thereby establishing fluid-tight seals at the diaphragm side of each of the flow regulator chips 187.

The exterior of the lid housing 157 may be selectively contoured, featuring external boss features corresponding to each internal O-ring cavity, and an elongated protrusion extending the full length of the lid housing corresponding to the internal reference cross-hole 179. This selective external geometry may thereby maintain a consistent, minimal wall thickness of, for example, approximately 0.3 mm around internal features, thereby minimizing titanium material volume while ensuring structural integrity.

Internal passages of the regulator assembly 155 and the housing of the regulator chips 158, according to an exemplary embodiment, may be further visualized in reference to the section views of FIGS. 17-19. Acting on each of the major faces of the regulator chips 158 may be O-rings, which may be under axial compression. Two port O-rings 159 may act against the inlet and outlet port side of the regulator chips 158, and a single diaphragm O-ring 160 may act against the diaphragm side of regulator chips 158. The O-ring compression may not only provide a sealed interface but also protect the regulator chips 158 from vibration and shock in the direction they are most sensitive.

In reference to FIGS. 20-21, which show the drug delivery system components of the system isolated from the non-delivery system components of the case according to an exemplary embodiment, the plug and socket interface between the reservoir assembly 139 and the regulator assembly 155 is also shown clearly. With respect to the reservoir assembly 139, the outlet tube 147 may be welded to header 101, and the adapter 148 may be welded to the outlet tube 147. The plug adapter 148 may be seated in the socket 167, with the adapter axial O-ring 183 seated in the counterbore 151 and the adapter radial O-ring 184 seated within the radial O-ring groove 150 of the plug adapter 148. These two O-ring seals may provide redundant sealing between the plug adapter 148 of the reservoir assembly 139 and the socket 167 of the regulator assembly 155.

To ensure that the adapter 148 remains seated in the socket 167 and the axial compression of axial O-ring 183 is maintained, a non-continuous laser weld may be achieved at the adapter weld seam 182 in areas where the outlet tube 147 does not obstruct weld access to the adapter weld seam 182.

With respect to the drug delivery system, in some embodiments, all components and interfaces located upstream from the regulators—where internal pressures are higher—may be enclosed within titanium housings that are hermetically-sealed, for example, by laser welding. These high-pressure regions may utilize robust sealing methods, such as a septum with a high-integrity seal or a dual O-ring configuration, as employed in the outflow adapter plug and socket interface with the regulator enclosure. In contrast, the downstream interfaces, which operate under lower pressure, may utilize barb-style connections. These barb interfaces may be mechanically reinforced using auxiliary retention methods such as sutures, collars, zip ties, crimps, or shrink tube segments to ensure secure, leak-resistant connections and mitigate the risk of disconnection or leakage under physiological loading conditions.

Figure 23:
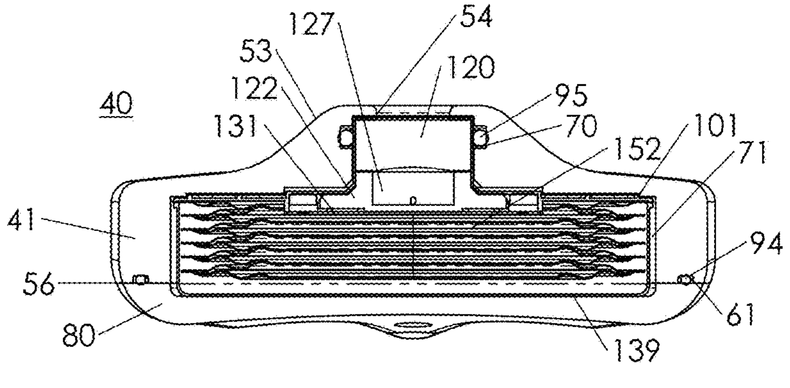
FIG. 23 is a sectional view of the integrated case assembly according to an exemplary embodiment, taken along the mid-plane of the reservoir assembly in a plane parallel to the short axis of the device.

Referring now to FIGS. 22-23, section views of an exemplary embodiment of the integrated assembly are shown along the long axis of the case and along the short axis, dissecting the reservoir assembly correspondingly. Internal components of the drug delivery system may include the reservoir assembly 139 and the regulator assembly 155. The cylindrical section of the reservoir assembly 139 may fit primarily within the cylindrical pocket 71 of the outer shell 41, and the tubular portion 103 of the header 101 may fit within the header socket 69 of the outer shell 41. With respect to axial accommodation, the reservoir assembly 139 may be held captive between the inner shell 80 and the outer shell 41, with some nominal clearance provided to account for tolerance variability.

The regulator assembly 155 may fit primarily within the posterior pocket 73 of the outer shell 41 between the reservoir assembly 139 and the perpendicular face 74. A small portion of the reservoir assembly 139 and the regulator assembly 155 may be accommodated in pocket 90 of the inner shell 80. The boundary of the posterior pocket region 73 of the outer shell 41 may be intentionally offset with respect to the flow regulator assembly 155. This design may accommodate variability in the tilt and position of the flow regulator assembly 155, which may be rigidly-affixed to the reservoir outlet tube 147. By providing clearance on all sides, the configuration may allow the flow regulator assembly 155 to "float" within the pocket prior to epoxy filling of the recesses and voids within the case. This floating condition may ensure that the outlet tube 147 and its welded connections are not subjected to significant mechanical stress during assembly, thereby preserving structural integrity and minimizing the risk of stress-induced failure.

The central slot 79 of the outer shell 41 may provide sufficient spatial clearance for the accommodation of the radial protrusion 107 of the header 101 and the outlet tube 147 of the reservoir assembly 139. According to an exemplary embodiment, the minimum thickness of outer shell 41 at central slot 79 may be approximately 1 mm, with other regions of the outer shell 41 may be much thicker.

The tubular portion 103 of the header 101 may be centralized within the palpable nub 53, utilizing the additional height for accommodating the septum 120 and the septum support insert 122 with the needle fill cavity 127 and the needle stop surface 128. These components may facilitate a refill port interface for filling the reservoir assembly 139 by advancing a non-coring needle through the orifice 54 and the septum 120 up against the needle stop surface 128 and injecting the drug into the needle fill cavity 127. As described previously, the needle fill cavity 127 may be in fluid communication with the drug reservoir 152 on account of passages and grooves in the septum support insert 122 and fluid communication holes in the retention plate 131. The titanium terminal wall 104 of the header 101 may be covered by the header liner 68 of the outer shell 41, which may be a sufficient wall to shield a needle from colliding with a hard metallic surface.

The section view of FIG. 22 further shows the interface of two case screws 98 and a fill port screw 99 at the posterior end of case 40, as well as several O-ring and gasket interfaces according to an exemplary embodiment. The case screws 98 may be inserted through the counterbores 84 of the inner shell 80 and bind up against the countersinks 93 when threaded into the threaded holes 62 of the outer shell 41. Instances of O-Rings 96 may be seated in the counterbore 63 of the outer shell 41 and may be compressed against the inner shell 80, whereas the counterbore 63 may control the extent of axial compression of each instance of the O-rings 96.

The gasket 94, which may surround all the internal cavities, may likewise be compressed within the gasket groove 61 when the inner shell 80 is secured against the outer shell 41, where the depth of the gasket groove 61 may control the axial compression of the gasket 94.

The O-Ring 95 may sit in the radial groove 70 of the outer shell 41 for maintaining a seal between the outer shell 31 and the tubular section 103 of the header 101 (integrated with the reservoir assembly 139).

In FIG. 22, near the posterior end 43 of the case 40, the posterior fill channel 65 may be seen adjacent to the posterior fill port screw 99 according to an exemplary embodiment. The two instances of the fill port screws 99 (only the posterior fill port is shown in FIG. 22, since the anterior fill port is not on the central plane) may be only engaged to the inner shell 80.

With seals provided at all the external seams and holes, the case, according to an exemplary embodiment, may be epoxy-filled through accessing port holes at the anterior and posterior ends of the case through the inner shell 80. With the fill port screws 99 removed, epoxy may be injected through one end while the internal air may be vented through the other, with the venting end held higher than the injection end, or through the use of vacuum infusion. Internal voids between the outer shell 41, the inner shell 80, and the internal drug delivery system components may thus be filled with liquid epoxy and then cured. Once the case assembly 40 is epoxy-filled, the fill port screw 99 may be advanced to engage the bottom of the proximal fill port counterbore 85. An additional counterbore for seating the O-ring 97 may be provided to establish an axial seal at fill ports when compressed by the button head of the fill port screw 99. Once the fill ports are sealed, all internal cavities within the case may be sealed off.

All openings of the external shell 41 and the internal shell 80, as well as the parting seam 56 between them, may be sealed with elastomers, including, for example, gaskets or O-rings positioned along the openings and outer boundaries of the case 40. These elastomeric seals may serve multiple functions: for example, they may provide a redundant barrier to prevent drug or propellant leakage in the event of a failure within the drug delivery system and ensure containment of any such leakage within the enclosure, thereby mitigating the risk of fluid escaping into the cranial cavity or contacting the patient's brain. Additionally, the seals may prevent epoxy from seeping out through the joints during assembly, enabling complete and controlled filling of the internal volume.

The case design may reinforce the thin-walled reservoir assembly 139, which, on its own, may not possess sufficient wall thickness to resist internal pressure loading without yielding. Accordingly, the pump housing may include a composite structure including both titanium and a biocompatible plastic (e.g., PEEK), to balance mechanical strength with MRI compatibility. By confining the reservoir assembly 139 (including the filling of any gaps with epoxy), the case may reinforce the thin-wall reservoir assembly 139 to prevent yielding and excessive displacement. Accordingly, the outer shell 41 and the inner shell 80 may be sufficiently thick and stiff to provide adequate reinforcement. The positions of the screws 98 around the reservoir assembly 139 may ensure that the stress is nearly equally distributed around its perimeter.

According to an exemplary embodiment, the minimum thickness of the outer shell 41 along the pseudo-exocranial surface 44 may be approximately 1 mm, and the minimum thickness of the inner shell 80 along the pseudo-endocranial surface 45 may be approximately 1 mm. However, the outer shell 41 and the inner shell 80 may become incrementally thicker with increased offset from the mid-plane, as shown in FIG. 22. The increased thickness at sections offset from the worst-case minimum mid-plane thickness may further reinforce the reservoir assembly 139 when pressurized. Furthermore, the placement of the screws 98 around the reservoir assembly 139 may ensure that stress is evenly distributed around the reservoir assembly 139 perimeter.

Figure 24:
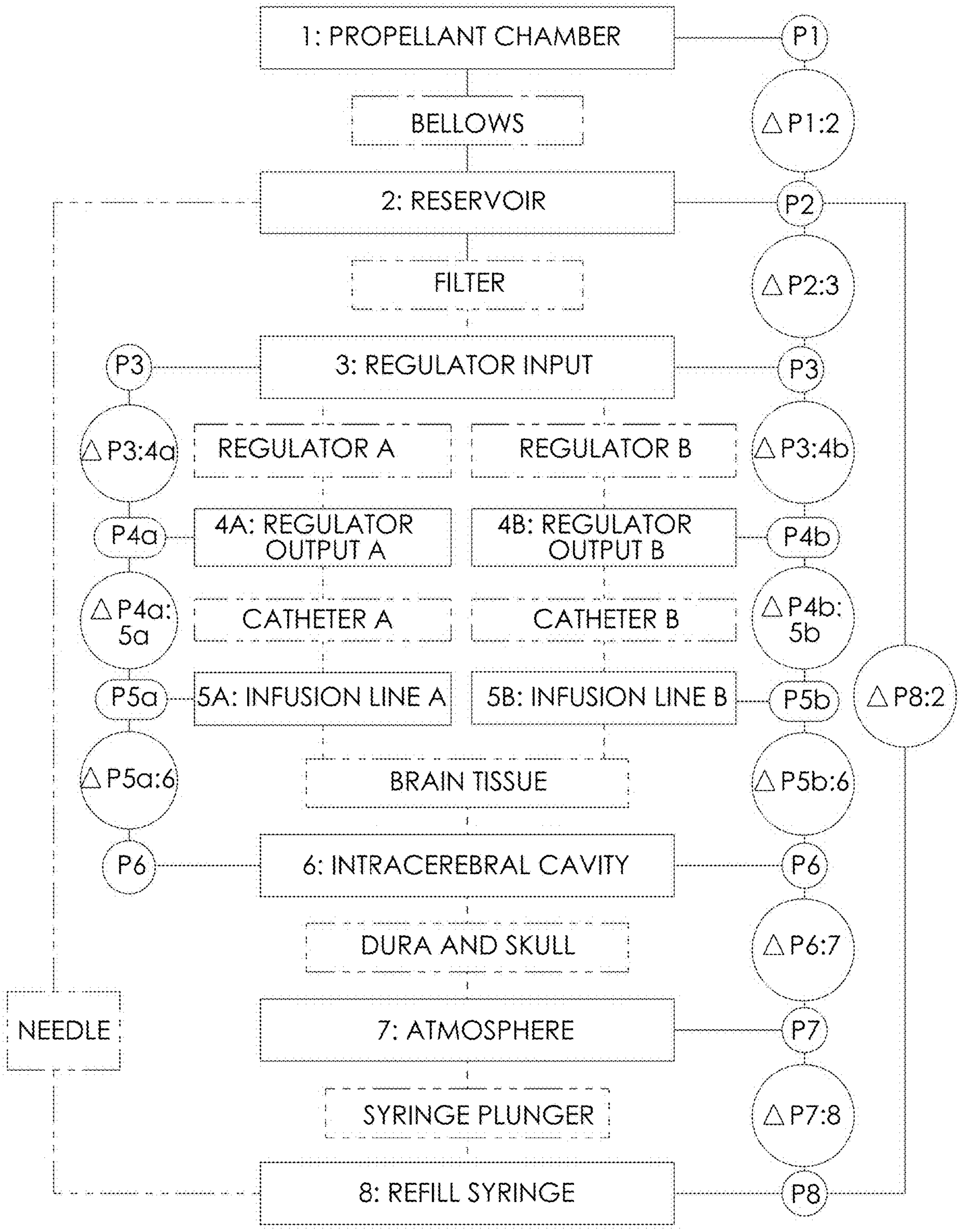
FIG. 24 is an exemplary system diagram illustrating relevant reference pressures and pressure differentials with respect to system chambers that exhibit various resistive elements between each other.

In reference to FIG. 24, a system diagram is shown, illustrating relevant reference pressures and pressure differentials with respect to system chambers that exhibit various resistive elements between them according to an exemplary embodiment. The system may be designed for various operating states in which the various pressures within the system can vary within an acceptable range. The states addressed in the design include at least the following.

Patient Use (State of Non-Infusion)—This state, alternatively described as non-infusion, describes the case when the Implantable System is implanted in the patient, but the Implantable Pump is not infusing. In this state, the bellows may have reached a mechanical limit.

Patient Use (State of Infusion)—This state, alternatively described as infusion, describes the case when the Implantable Pump is infusing Drug into the patient via the displacement of the bellows. In this operating state, the amount of deliverable Drug in the Implantable Pump may change.

Withdraw—This state, a subset of Implantable Pump Rinse, Flush, and Dose, describes the case when the clinician is removing Drug from the Implantable Pump for the purposes of rinsing the fluid path, flushing saline through the fluid path, or dosing the patient. As mentioned above, it may be understood that design elements included here may minimize dead volume and mitigate risk for mixing old medicine with newly-injected medicine.

Fill—This state, a subset of Implantable Pump Rinse, Flush, and Dose, describes the case when the clinician is adding Drug to the Implantable Pump for the purposes of rinsing the fluid path, flushing saline through the fluid path, or dosing the patient.

Sterilization—This state describes the case when the Implantable Pump undergoes steam sterilization.

Transport—This state, a subset of Transport & Storage, describes the case when the Implantable Pump is shipped between sites where it is stored or used.

Storage—This state, a subset of Transport & Storage, describes the case when the Implantable Pump is stored before use.

Pre-Implantation Surgical Handling—This state, alternatively described as preparation, describes the case when the surgeon first implants the Implantable System in the patient.

During Sterilization, Transport, Storage, and Pre-Implantation Surgical Handling, the reservoir may not be filled with fluid, allowing the bellows to fully compress (propellant to expand). During sterilization, the case may be subjected to the maximum temperature and may withstand the corresponding worst-case pressure applied by the propellant in the vapor phase.

The relevant pressures and pressure differentials may include the following:

P7 is the atmospheric pressure, which is the absolute pressure in the surrounding atmosphere. Preparation, refill, and infusion may be able to happen in a wide range of weather conditions, including low-pressure and high-pressure systems. The patient may not be permitted to be submerged or receive hypobaric treatment during preparation, refill, or infusion. The patient may travel by only ground transportation during infusion. This may lead to an estimated atmospheric pressure range during preparation, refill, or infusion of 950 to 1050 mbar.

During a state of non-infusion, the patient may travel to any location with an altitude ranging from sea level to +3000 meters. They may encounter a wide range of weather conditions, including low-pressure and high-pressure systems. The patient may travel by air, surface vessel, or ground travel. The patient may bathe or swim on the surface but may not dive deeper than 1 meter below the surface of the water. The patient may not be permitted to receive hypobaric treatment, scuba dive, or travel by submersible. Under such conditions, this may lead to an estimated atmospheric pressure range during a state of non-infusion of 700 to 1300 mbar.

P1 is the propellant pressure, which is the absolute pressure in the propellant chamber. P1 is a function of temperature and drug volume. Temperature changes the vapor pressure of the two-phase fluid. The effect of drug volume may be minimized by the phase change of the propellant, which may maintain its pressure irrespective of the volume as long as some of it remains in both gas and liquid phases. Any contaminants, such as air and water, may change this behavior. As a result, measures may be taken during the propellant fill process to minimize contamination. For the sake of this analysis, an embodiment of a pure two-phase propellant (R-1233zd) with no volume-dependent pressure characteristics may be considered.

According to an exemplary embodiment, the volume of propellant may be engineered so that the propellant fully vaporizes when the temperature exceeds 41° C., which may minimize the pressure induced by high temperatures during transport and sterilization. During normal operation, including the states of refill, infusion, and non-infusion, the temperature of the implant may be 38.5±2.5° C. The implant may be safe under these conditions in an expanded implant temperature range of $$38.5^{+2.5}_{-7.5}\,^{\circ}\text{ C.}$$

ΔP1:2 is the differential pressure from the below exemplary assembly, which is the differential pressure between the propellant chamber and the drug chamber. The system may include a bellows assembly that hermetically separates the propellant from the drug. This may permit the transmission of pressure between the drug and the propellant. The bellows assembly may have a differential pressure across it, which results from the mechanical stiffness of the bellows material and its housing. This differential pressure may be a function of the volume of the drug in the bellows chamber.

The differential pressure may have three distinct regions: an empty knee, a linear region, and a full knee. During the two knees, the stiffness of the structures is dominated by the mechanical interference of the bellows and its two end stops. This leads to non-linear behavior. During the linear region, there is no interference between the bellows and the end stops. Therefore, the differential pressure may be understood to be solely a result of the spring rate of the bellows and can be modeled accordingly.

During refill and infusion, the bellows assembly may transition through its full travel, moving through the full knee, linear, and empty knee conditions. According to an exemplary design, while fully compressed, the bellows induces a differential pressure of 116±30% mbar (which means there is a higher pressure outside the bellows than inside). When fully extended, the bellows induces a differential pressure of −27±30% mbar (which means there is a higher pressure inside the bellows than outside).

ΔP7:8 is the differential pressure from the refill syringe, which is the differential pressure between atmospheric pressure and the refill syringe. During refill, there may be a pressure communication between P7 (atmospheric pressure) and the drug in the syringe (P8).

During refill there may be pressure communication between the atmosphere, at P7, and the refill syringe. This differential pressure may be different during a fluid removal process and a fluid fill process. During a fluid removal process, the syringe barrel may have a vented cap and ΔP7:8=0. During the fluid fill process, the syringe barrel pressure (P8) may be limited to 2000 mbar by an overpressure valve on the refill kit.

During refill, and only during refill, there may be pressure communication between the refill syringe, at pressure P8, and the drug chamber via the refill kit. This differential pressure may be different during a fluid removal process (when P2>P8) than during a fluid fill process (when P8>P2) and is defined by ΔP7:8 as P7 is fixed.

In both cases, this pressure differential can be modeled as a flow restriction. In the withdrawal state, it results from the flow restriction of the refill needle/extension tube in series with a partially-open stopcock. In the filling state, it results from the flow restriction of the refill needle/extension tube in series with the external filter.

P8 is the refill syringe pressure, which is the absolute pressure in the refill syringe.

ΔP8:2 is the differential pressure from refill access, which is the differential pressure across the needle and other refill access accessories.

P2 is the absolute pressure in the drug chamber. The driving parameters for P2 may depend on the state-whether it is a state of refill, infusion, or non-infusion. During a state of non-infusion, the bellows may have reached a mechanical limit. At that point, there is no pressure communication between the drug and the propellant, and there is no fluid flow, so P2=P3=P4=P5=P6.

During a state of refill, the pressure in the drug chamber is driven by the refill system. Therefore, P2=P7+ΔP7:8+ΔP8:2.

During a state of infusion, the pressure in the drug chamber is driven by the propellant chamber. Therefore, P2=P1+ΔP1:2.

During a state of non-infusion, the pressure in the drug chamber is driven by the downstream pressure, wherein P2=P6=P7+ΔP7:6.

P3 is the pressure upstream of the flow regulator, which is the absolute pressure immediately upstream of the flow regulator. P3 may therefore be driven by the propellant pressure, the refill kit, or the outlet pressure, depending on the conditions. During a state of infusion or refill, P3=P2+ΔP2:3. P3 may be driven by the propellant and/or the refill kit as described above. During a state of non-infusion, there is no flow through the fluid path, and P3=P6=P7+ΔP7:6.

ΔP6:7 is the intracranial differential pressure, which is the differential pressure between the atmosphere and the bulk cerebrospinal fluid. Intracranial pressure (ICP) may be understood to be a common term in clinical practice to describe the differential pressure between cerebrospinal fluid (CSF) and atmospheric pressure. The body maintains this pressure by regulating the amount of CSF in the skull. ICP is dependent on clinical conditions and patient behavior. It may typically range between 9 mbarg and 33 mbarg. ΔP6:7 (ICP) outside of this range may require medical intervention.

P6 is the brain pressure, which is the absolute pressure in the bulk cerebrospinal fluid.

ΔP5:6 is the Convective Pressure Gradient, which is the differential pressure between the catheter tip and bulk cerebrospinal fluid. Each infusion point will exhibit a slightly different convective pressure gradient (ΔP5a: 6 and ΔP5b: 6). During infusion, the device generates a pair of pressure gradients (ΔP5a: 6 and ΔP5b: 6) within the brain between the catheter outlets and lower pressure regions of the brain.

This pressure gradient may drive fluid flow through brain tissue in a manner such as convection-enhanced delivery, which may be modeled as a poroelastic solid. This means that there is a non-linear relationship between pressure and flow, as increased flow rates alter the pore structure of the brain. The expected range of convective pressure gradients during intraparenchymal infusion may be between 8 and 97 mbarg.

When in a state of non-infusion, there is no flow and no pressure drop, so ΔP5a: 6=ΔP5b: 6=0

P5 is the infusion line pressure, which is the absolute pressure at the catheter tip. Each catheter tip may have a slightly different differential pressure (P5a and P5b).

P4 is the pressure downstream of the flow regulator, which is the absolute pressure immediately downstream of the flow regulator. Each flow regulator may have a slightly different downstream pressure (P4a and P4b).

ΔP4:5 is the fluid outlet differential pressure, which is the differential pressure across the fluid outlet, including the catheter or catheters. Each catheter will have a slightly different outlet differential pressure (ΔP4:5a and ΔP4:5b). The device may include a fluid outlet that consists of fittings and a catheter(s). These may induce a pressure drop in the fluid path. The pressure drops across these components may be small and can be assumed to be 0. These may increase substantially in the event of a catheter obstruction and can change based on clinical conditions.

During a state of non-infusion, there is no fluid flow and P4a=P4b=P6=P7+ΔP6:7. During a state of infusion, including refill, the pressure downstream of the regulator can be expressed as $$P4a = P7 + \Delta P7{:}6 + \Delta P5a{:}6a + \Delta P4a{:}5a$$

$$P4b = P7 + \Delta P7{:}6 + \Delta P5b{:}6b + \Delta P4b{:}5b$$

ΔP2-3 is the differential pressure across the filter, which is the differential pressure across the internal filter. Downstream of the flow regulator, the pressure may depend on the amount of fluid flowing through the system.

ΔP3:4 is the differential pressure across the flow regulator, which is the differential pressure(s) across a flow regulator. Each flow regulator may have a slightly different differential pressure (ΔP3:4a and ΔP3:4b). The differential pressure across the flow regulator may determine the flow rate of a drug through the system. Notably, different medicines may require different flow rates and so a variety of flow regulators (ranging from low flow to high flow) may be used in different embodiments.

If this differential pressure is negative, i.e., the pressure is higher at the regulator output than the input, there may be backflow. According to an exemplary embodiment, if this differential pressure is between zero and +200 mbarg, forward flow may be regulated at about 0-2 μL/min. If this differential pressure is between +200 and +1200 mbarg, forward flow may be regulated between 2 and 4 μL/min. Flow regulator chips may be designed so that the flow rate never exceeds 10 μl/min in a plausible overpressure condition.

When in a state of non-infusion, there may be no flow and no pressure drop, so $$\Delta P3{:}4a = \Delta P3{:}4b = 0.$$

When in a state of infusion:

$$\Delta P3{:}4a = P4a - P3 = (P7 + \Delta P6{:}7 + \Delta P5a{:}6 + \Delta P4a{:}5a) - (P1 + \Delta P1{:}2 + \Delta P2{:}3).$$

$$\Delta P3{:}4b = P4b - P3 = (P7 + \Delta P6{:}7 + \Delta P5b{:}6 + \Delta P4b{:}5b) - (P1 + \Delta P1{:}2 + \Delta P2{:}3).$$

When in a state of refill:

$$\Delta P3:4a = P4a - P3 = (P7 + \Delta P6{:}7 + \Delta P5a{:}6 + \Delta P4a{:}5a) - (P7 + \Delta P7{:}8 + \Delta P8{:}2 + \Delta P2{:}3).$$

$$\Delta P3:4b = P4b - P3 = (P7 + \Delta P6{:}7 + \Delta P5b{:}6 + \Delta P4b{:}5b) - (P7 + \Delta P7{:}8 + \Delta P8{:}2 + \Delta P2{:}3).$$

The foregoing analysis of system pressures and differentials in various operating states underscores the complexity and precision required for safe and effective operation of the Implantable System. Each state (whether functional, procedural, or logistical) introduces specific environmental and physiological boundary conditions that influence the pressure dynamics across chambers and resistive elements. By modeling the system under these diverse conditions, the design may ensure consistent drug delivery performance, provide safeguards against adverse pressure scenarios, and accommodate the full lifecycle of use, from manufacturing and sterilization through long-term implantation. The comprehensive mapping of pressures provides a foundational basis for further system optimization, validation, and regulatory compliance.

Figure 25:
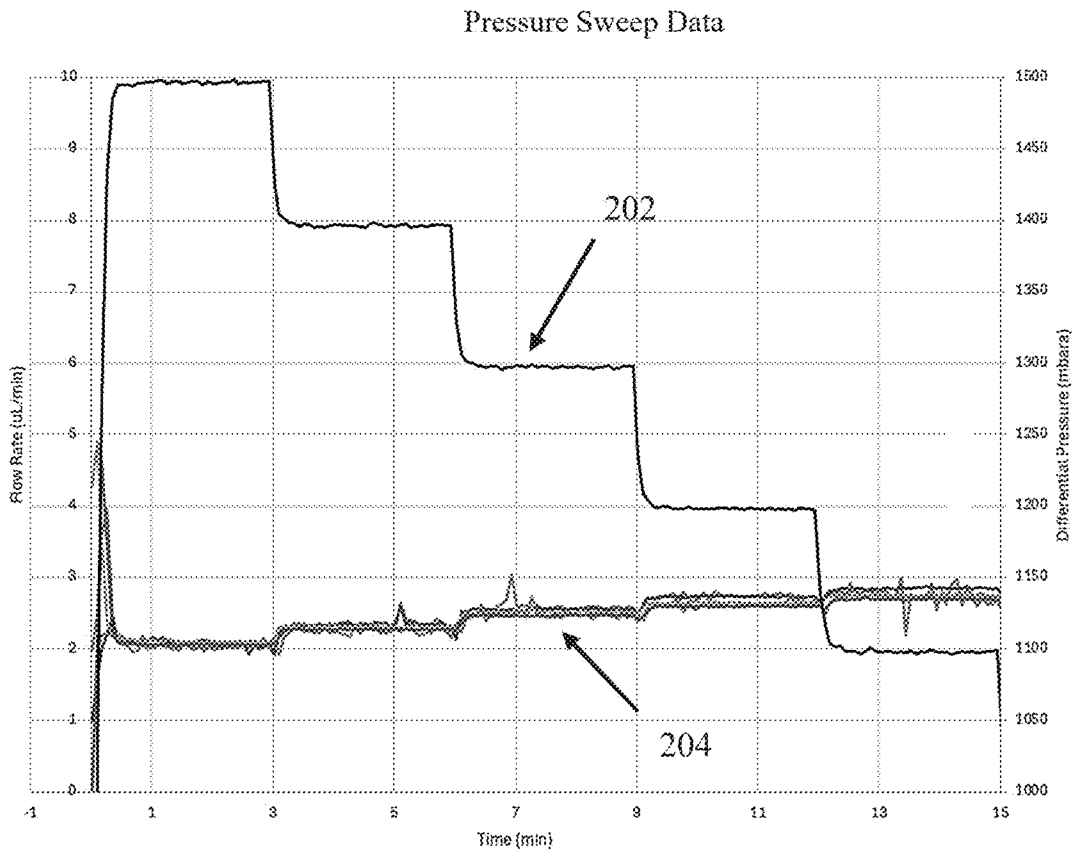
FIG. 25 is experimental pressure sweep data with an exemplary embodiment of a medical implant such as shown in FIGS. 1-24 and utilizing a regulator.
Figure 26A:
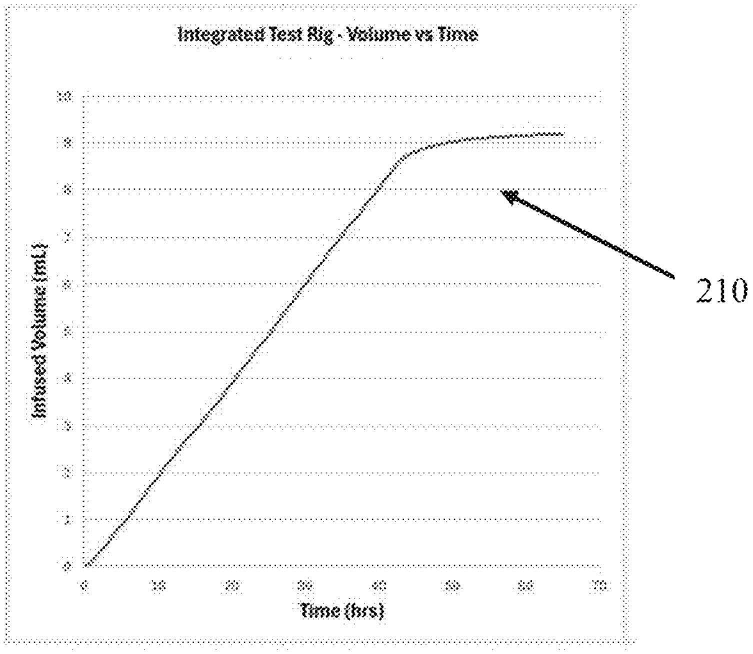
FIG. 26A is experimental volume vs time data with an embodiment of a medical implant such as shown in FIGS. 1-24 and utilizing a regulator.
Figure 26B:
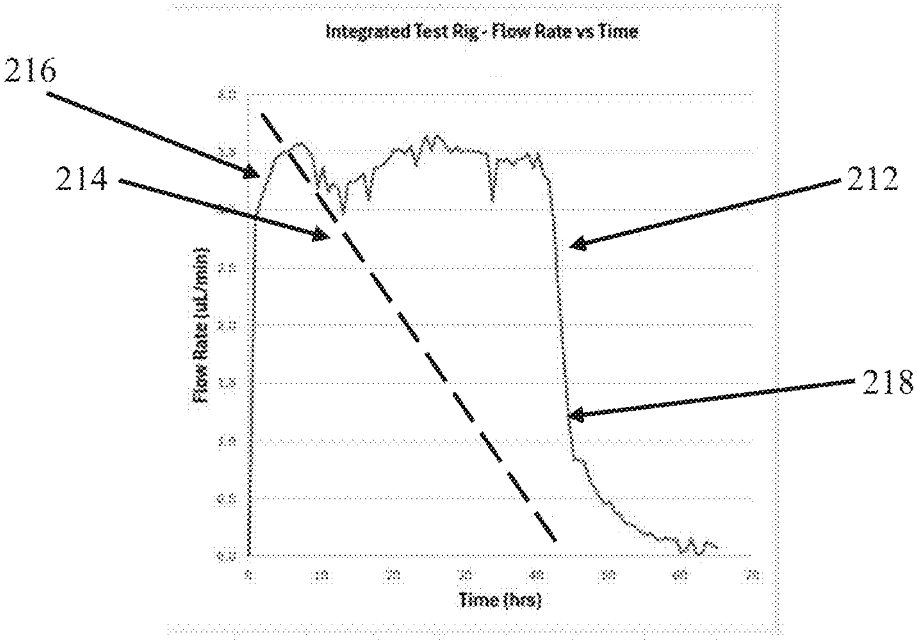
FIG. 26B is experimental flow rate vs time data with an embodiment of a medical implant such as shown in FIGS. 1-24 and utilizing a regulator.

In reference to FIG. 25-26B, experimental data with an embodiment of a medical implant such as shown in FIGS. 1-24 and utilizing a regulator, as described above, may be shown and described. The data may be understood to be with respect to an integrated fluid path of a whole pump including bellows assembly. Referring to FIG. 25 a differential pressure 202 may be shown over time, which may be understood to demonstrate changing pressure conditions in the medical implant. A plurality of flow rates 204 may further be shown according to a plurality of trial runs and corresponding to the changing differential pressure 202. It may be understood that as the pressure changes the relative flow rate remains within a regulated band.

Referring to FIGS. 26A & 26B, experimental data of an infused volume 210 and a corresponding flow rate 212 over time may be shown. For comparison a flow rate over time based on a restrictor 214 may be shown. The data may be understood to show when a drug reservoir is full 216 and when the drug reservoir is empty 218.

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A craniofacial medical implant housing comprising: a high-profile reconstructive implant configured to replace missing bone or soft tissue in a temporal location;

a two-phase propellant, wherein the two-phase propellant is Trans-1-chloro-3,3,3-trifluoropropene and has a vapor pressure of less than 45 PSI at a body temperature;

a pump configured to maintain a regulated infusion flow rate of a fluid via the two-phase propellant; and at least one catheter configured to deliver the fluid from the reconstructive implant to a target site.

2. The medical implant housing of claim 1, wherein the reconstructive implant is a craniofacial implant configured to augment or restore a contour in a craniomaxillofacial area.

3. The medical implant housing of claim 1, wherein the reconstructive implant comprises at least a biocompatible plastic outer housing; and wherein the reconstructive implant is configured to minimize MRI-artifact of the medical implant housing.

4. The medical implant housing of claim 3, wherein the biocompatible plastic outer housing further comprises at least polyether ether ketone (PEEK).

5. The medical implant housing of claim 1, wherein the pump comprises a composite structure of at least titanium and plastic.

6. The medical implant housing of claim 1, wherein the pump further comprises a filter configured to prevent bacteria and particles from reaching the target site.

7. The medical implant housing of claim 6, wherein the filter comprises sintered titanium.

* * * * *